(12) United States Patent
Hong et al.

(10) Patent No.: US 10,191,040 B2
(45) Date of Patent: Jan. 29, 2019

(54) METHOD OF MULTIPLEX IMMUNOASSAYS UTILIZING DIFFERENTIAL AFFINITY AND METHODS FOR SYNTHESIZING APTAMER-BASED REAGENTS FOR MULTIPLEX IMMUNOASSAYS

(71) Applicants: Chin-Yih Hong, Changhua (TW); Herng-Er Horng, New Taipei (TW)

(72) Inventors: Chin-Yih Hong, Changhua (TW); Herng-Er Horng, New Taipei (TW)

(*) Notice: Subject to any disclaimer, the term of this patent is extended or adjusted under 35 U.S.C. 154(b) by 0 days.

(21) Appl. No.: 15/281,077

(22) Filed: Sep. 30, 2016

(65) Prior Publication Data

US 2018/0095078 A1    Apr. 5, 2018

(51) Int. Cl.

| | |
|---|---|
| *G01N 33/53* | (2006.01) |
| *C40B 40/06* | (2006.01) |
| *C12N 15/10* | (2006.01) |
| *C12N 15/115* | (2010.01) |
| *C12Q 1/68* | (2018.01) |
| *G01N 33/543* | (2006.01) |
| *C12Q 1/6811* | (2018.01) |

(52) U.S. Cl.
CPC ... *G01N 33/54333* (2013.01); *C12N 15/1013* (2013.01); *C12N 15/1072* (2013.01); *C12Q 1/6811* (2013.01); *C40B 40/06* (2013.01); *G01N 33/5308* (2013.01)

(58) Field of Classification Search
None
See application file for complete search history.

(56) References Cited

U.S. PATENT DOCUMENTS

2013/0210023 A1*   8/2013   Tanner ............... C12Q 1/6893
                                                          435/6.15
2015/0119285 A1    4/2015   Hong et al.

* cited by examiner

*Primary Examiner* — Richard A Schnizer
(74) *Attorney, Agent, or Firm* — JCIPRNET

(57) ABSTRACT

Multiplex immunoassays utilize the differential affinities among the conjugation pairs between the capture ligands and target analytes are proposed. Window magnetic-assisted rapid aptamer selection (window-MARAS) methods for selecting aptamers with desirable affinity toward the target analytes and methods for generating reagents for multiplex immunoassays or multiplex detection in one assay by utilizing the selected aptamers as capture ligands in reagents are described and used to demonstrate the feasibility of multiplex immunoassays based on the differential affinity of conjugation pairs between the capture ligands and target analytes.

12 Claims, 15 Drawing Sheets

Specification includes a Sequence Listing.

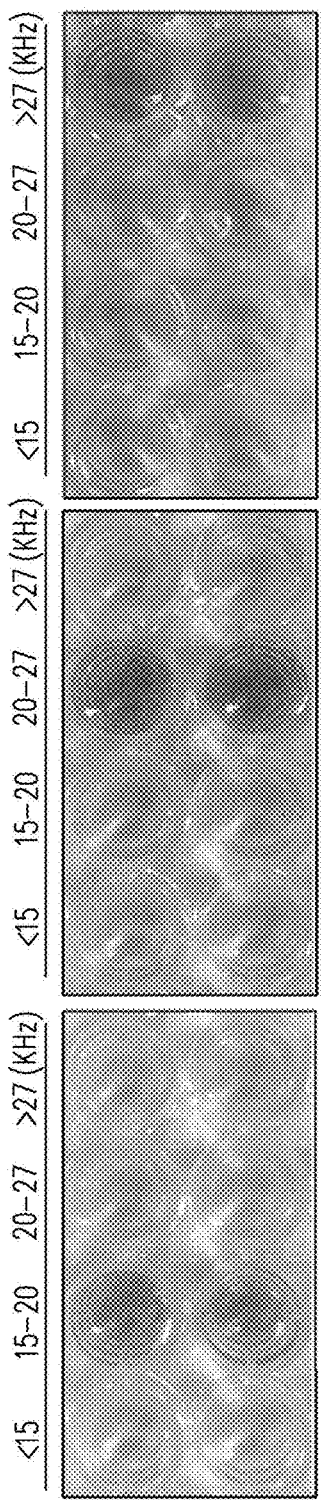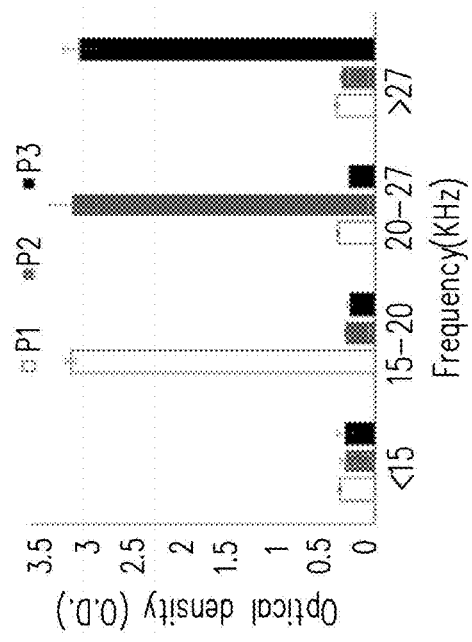
FIG. 8A
FIG. 8B
FIG. 8C
FIG. 8D

METHOD OF MULTIPLEX IMMUNOASSAYS UTILIZING DIFFERENTIAL AFFINITY AND METHODS FOR SYNTHESIZING APTAMER-BASED REAGENTS FOR MULTIPLEX IMMUNOASSAYS

BACKGROUND

Technical Field

The present invention generally relates to a method of multiplex immunoassay utilizing differential affinity and methods for generating aptamer-based reagents for multiplex immunoassay. Particularly, the present invention relates to a magnetic-assisted differential affinity selection method for generating aptamer-based reagents and a method of multiplex immunoassays using aptamer-based reagents utilizing differential affinity.

Related Art

Multiplex immunoassays have been widely used in basic biomedical research due to their ability in performing a large number of different assays all in a single reaction vessel from a relatively smaller sample volume with high efficiency. In multiplex immunoassays, high-affinity, high specificity capture ligands are immobilized in parallel arrays in either planar arrays or on encoded microspheres. When incubating with samples, target analytes are bound to corresponding capture ligands, respectively, and form ligand-target complexes. After washing to remove unbound substances, reporter ligands conjugated with detection labels are attached to the bound complexes. Then a detection means is used to quantify the detection labels, which is then converted to the mass concentration of the target analyte using a pre-determined calibration curve. The number of target analytes can be analyzed is up to hundreds in a single experiment. Therefore, multiplex immunoassays become powerful analytic tools in basic biomedical research. However, beside its complexity and expensiveness, numerous problems and challenges still exist, including the availability of a large number of highly specific capture ligands for a wide range of analytes, cross-reactivity between capture ligands and analytes and assay diluents, interference from matrix effect, the required compromise of the assay parameters when developing multiple assays, and the requirement for pre-labelling reporter molecules for detection.

On the other hand, multiplex immunoassays also become important for clinical diagnostic purposes for its ability of identifying multiple biomarkers for a wide range of diseases. Even though the multiplex immunoassay is able to analyze up to hundred analytes in one assay, it only requires a few biomarkers for disease diagnosis (ideally four biomarkers at most). It is desirable to develop a multiplex immunoassay platform specifically for clinical applications.

Aptamers including binding pockets bind with high specificity and affinity to a variety of target analytes, diversified from micro-molecules (such as organic molecules, ions, peptides, proteins, nucleic acids), macro-molecules to even whole cells, viruses, parasites or tissues. Once the sequence of aptamer is identified for the target analytes, the entire aptamer can be produced by chemical synthesis. Furthermore, aptamers modified with functional groups can increase their stability in various biological applications, but may be harmful for nucleic acids. Aptamers not only have the potential to be an excellent tool to target pathogenic and malignant cells or tissues and substitute antibodies but also can be applied on purification, diagnostics, biosensors and anti-infectious agents. As the aptamers are potential in many aspects, an efficient selection method, Magnetic-Assisted Rapid Aptamer Selection (MARAS), has been developed which is straightforward enough to rapidly screen suitable aptamers with high affinity and specificity for their target analytes.

SUMMARY

Some aspects of the present invention relate to the multiplex immunoassays utilizing the differential affinity among capture ligand(s) and corresponding target analyte(s). Some aspects of the present invention relate to methods for synthesizing aptamer-based reagents capable of performing multiplex detection in one assay. Also, some aspects of the present invention relate to a multiplex immunoassay platform specifically for clinical application, utilizing differential affinity using aptamer-based reagents, with low costs, easy to operate, and quick assaying time.

Some aspects of the present invention provide methods for detecting and/or quantitating multiple analytes in a single assay, particularly multiple-analyte assays based on differential affinity (binding force). The assay of this invention employs the differential affinity of the conjugation pairs among the capture ligands and target analytes to differentiate and quantify different captured analytes in a test sample.

Some aspects of the present invention relate to the methods for selecting a single aptamer having desired affinity toward different target analytes using window magnetic-assisted rapid aptamer selection (window-MARAS), synthesizing the aptamer-based reagent capable of performing multiplex detection in one assay, and detecting and quantitating multiple analytes in samples using the aptamer-based reagent. The window-MARAS is a MARAS procedure with a lower-bound and an upper-bound frequencies/strengths of externally applied oscillating magnetic fields to select aptamers having a desired affinity range toward the target analyte from an oligonucleotide library.

Some aspects of the present invention relate to the methods for selecting different aptamers having desired affinity toward their corresponding analytes using window-MARAS, synthesizing the aptamer-based reagent capable of performing multiplex detection in one assay, and detecting and quantitating multiple analytes in samples using the aptamer-based reagents.

The present invention provides an aptamer selection method utilizing biofunctionalized magnetic particles to screen the oligonucleotides capable of binding to the target analytes from the DNA library.

The present invention provides an affinity differentiating means utilizing biofunctionalized magnetic particles coupled with externally applied oscillating magnetic field to differentiate the affinity of conjugation pairs between aptamer(s) and target analyte(s) in a sample during multiplex immunoassay.

In order to make the aforementioned and other features and advantages of the disclosure comprehensible, several exemplary embodiments accompanied with figures are described in detail below.

BRIEF DESCRIPTION OF THE DRAWINGS

The accompanying drawings are included to provide a further understanding of the disclosure, and are incorporated in and constitute a part of this specification. The drawings illustrate embodiments of the disclosure and, together with the description, serve to explain the principles of the disclosure.

FIG. 8A-8C show the duplicate photo images (upper and lower rows) for the validation of MP-1 aptamer conjugating multiple target analytes with differential affinity by aptamer-based ELISA according to some embodiments of the present invention.

FIG. 8D shows the measured optical density of control, P1, P2, and P3.

DETAILED DESCRIPTION OF DISCLOSED EMBODIMENTS

Some aspects of the present invention relate to the multiplex immunoassays utilizing the differential affinity among capture ligand(s) and corresponding target analyte(s). Some aspects of the present invention relate to window-MARAS methods for selecting a single aptamer having differential affinity toward the different target analytes. Some aspects of the present invention relate to window-MARAS methods for selecting aptamers with desirable affinity toward the analytes. Some aspects of the present invention relate to methods for generating reagents for multiplex immunoassays or multiplex detection in one assay by utilizing the selected aptamers as reagents. Also, some aspects of the present invention relate to a method for detecting and determining the quantities of multiple target analytes in a sample using the synthesized aptamer-based reagents.

Figure 1:
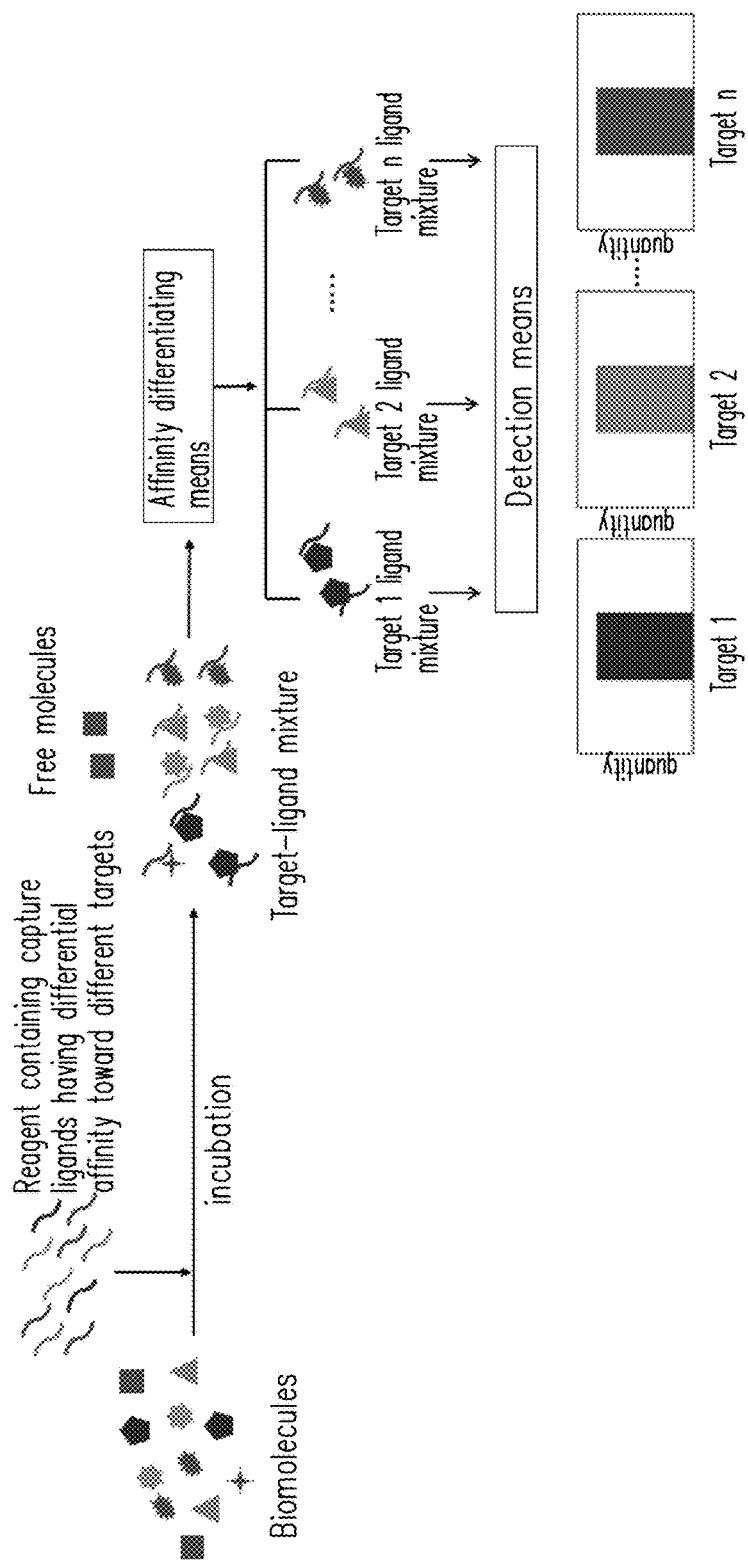
FIG. 1 schematically illustrates the method of multiplex immunoassays utilizing differential affinities among the capture ligands and target analytes according to some embodiments of the present invention.

In general, the affinity of the conjugation pair ranges from hundred nanomolar to lower picomolar in term of equilibrium dissociation constant. By carefully choosing the conjugation pair with the desired affinity for the capture ligands toward the target analytes, such that the binding strengths of conjugation are different among the different group of capture ligands and target analytes in multiplex assay, and applying an affinity differentiating mechanism to distinguish the different conjugation pairs, multiplex immunoassays can be realized. FIG. 1 schematically illustrates the concept of multiplex immunoassay utilizing the differential affinity among the conjugation pairs between the capture ligands and target analytes in a sample. Generally, the capture ligands are applied to the multiplex immunoassay for detecting or quantifying the target analytes in the sample. After mixing and incubating, various capture ligands and the corresponding target analytes (biomolecules) in the sample form ligand-analyte complexes, also called conjugation pairs. Dependent on the capture ligand and target analyte of the conjugation pair, different types of the conjugation pairs have different binding strengths or different affinities. Later, the ligand-analyte complexes are subjected to an affinity differentiating means to differentiate different types of the conjugation pairs by their different binding affinities. The conjugation pairs, formed by the capture ligands and captured analytes, include, but are not limit to, pairs of antibody-antigen, DNA/RNA aptamer-captured analyte, and DNA/RNA sequence(s) to its complemental sequence(s) (nucleic acid hybridization). In certain embodiments a capture ligand can specifically bind to a single target analyte. In other embodiments the capture ligand may be able to bind to multiple target analytes. The former case means that one type of the capture ligand can only specifically bind to its corresponding target analyte. The latter case means that one type of capture ligand can specifically bind to multiple target analytes, separately or simultaneously. Each type of conjugation pairs has different binding strength dependent on the capture ligand and target analyte forming the pair. Moreover, the capture ligands include, but are not limit to, antibodies (such as polyclonal antibodies, monoclonal antibodies, single-chain antibodies, chimeric antibodies, humanized antibodies, and antibody fragments), nucleotides (such as oligonucleotides, polynucleotides, nucleic acids, nucleic acid ligands, DNA/RNA aptamers) and any other known ligand that can bind to at least one target analyte. In addition, the target analytes include, but are not limit to, antigens of all types, such as proteins, polysaccharides, and small molecules coupled to a protein, peptides, nucleic acids (DNA and RNA), carbohydrates, antibiotics, organic molecules, ions, cells, viruses, parasites or tissues. The affinity differentiating means used to distinguish the conjugation pairs provides an affinity differentiating mechanism and include, but are not limit to, mechanical force (for example, stretch force induced by motion of ligand-analyte complex in the case the complex is freely suspended in an aqueous solution such as magnetic particles conjugated with ligand-analytes drove by oscillating magnetic field in an aqueous solution, hydrodynamic force induced by stringent washing in the case the complex is attached to a fixed substrate or trapped such as fluidic channels, and centrifugal force induced by spinning the ligand-analyte complex attached to a fixed substrate or trapped such as fluidic channel in a lab-on-a-disc), electromagnetic force (for example, static magnetic force induced by magnetic gradient field in the case magnetic substances are used and static electric force induced by electric field in the case electrically charged substances are used), or any combination of above. To implement the affinity differentiating mechanisms, stretch forces by varying magnetic particle motion in aqueous solution, hydrodynamic forces by varying washing buffer velocity in fluidic channel, centrifugal forces by spinning the disc at different spin rate, and electromagnetic forces by varying the strength of magnetic gradient field and/or electric field can be used. It is noted that the affinity differentiating mechanisms can also be used to select the conjugation pair having desired affinity ranges as well as to distinguish the conjugation pair of the ligand-analyte complex during the detection and quantification stages.

Generally, the support types of immunoassays suitable for the embodiments of the invention include solid-support immunoassays, moveable-support immunoassays and combined-support immunoassays. For a solid-support immunoassays, capture ligands or target analytes are linked and fixed to a surface, then the target analytes/capture ligands are respectively conjugated to the capture ligands/target analytes, thus forming ligand-analyte complexes. For a moveable-support immunoassays, micro or nano particles are used to replace the fixed surface, and the ligand-analyte complexes are bound on the surface of the particles forming ligand-analyte-particle or analyte-ligand-particle complexes of which magnetic or electric fields can be used to manipulate the ligand-analyte-particle/analyte-ligand-particle complexes if magnetic particles or dielectric particles are used, respectively. During some process of immunoassay (for example the washing step or separation step), the particles used for movable-support immunoassays are freely suspended and moveable in an aqueous solution and optionally collected by various collecting means, such as using a permanent magnet to catch or collect the magnetic particles, an electric field to catch dielectric particles, or a geometric shape to trap particles, and such immunoassays are referred to as combined-support immunoassays.

To detect and quantify the analytes in the sample in certain embodiment of this invention, reporter ligands conjugated with a label or tag are used. The reporter ligands are bonded to the ligand-analyte complexes and the detection means is employed to measure the quantity of the labels. In another embodiment of this invention, there is no need for reporter ligands and/or labels, such as for label-free assays. Generally, the conjugation between the capture ligand, target analyte and/or reporter ligand with or without the label or tag can be classified into three types: direct, sandwiched and competitive types, like those practices commonly used in ELISA. This invention is directed to multiplex immunoassays utilizing differential affinity, and any workable detection method or conjugation type known to the artisans in the field of immunoassays can be employed, not intended to limit the detection method or conjugation type. The measured quantities are then converted to the mass concentration/quantities of the analytes via a predetermined calibration curve. The labels are, but not limited to, a radio-active material, an enzyme, a liposome-based label, a chromophore, a fluorophore, a dye, or a combination thereof. In other embodiments of this invention, no reporter ligands is used, of which the labels are directly conjugated to the capture ligands. The detection methods suitable for use with the present invention include, but are not limited to, optical/fluorescence detection, radiochemical detection, electrochemical detection, impedance detection, magnetic detection provided that magnetic particles are used as moveable support for the ligand-analyte complexes, or any detections commonly used in biomedical assays.

Figure 2:
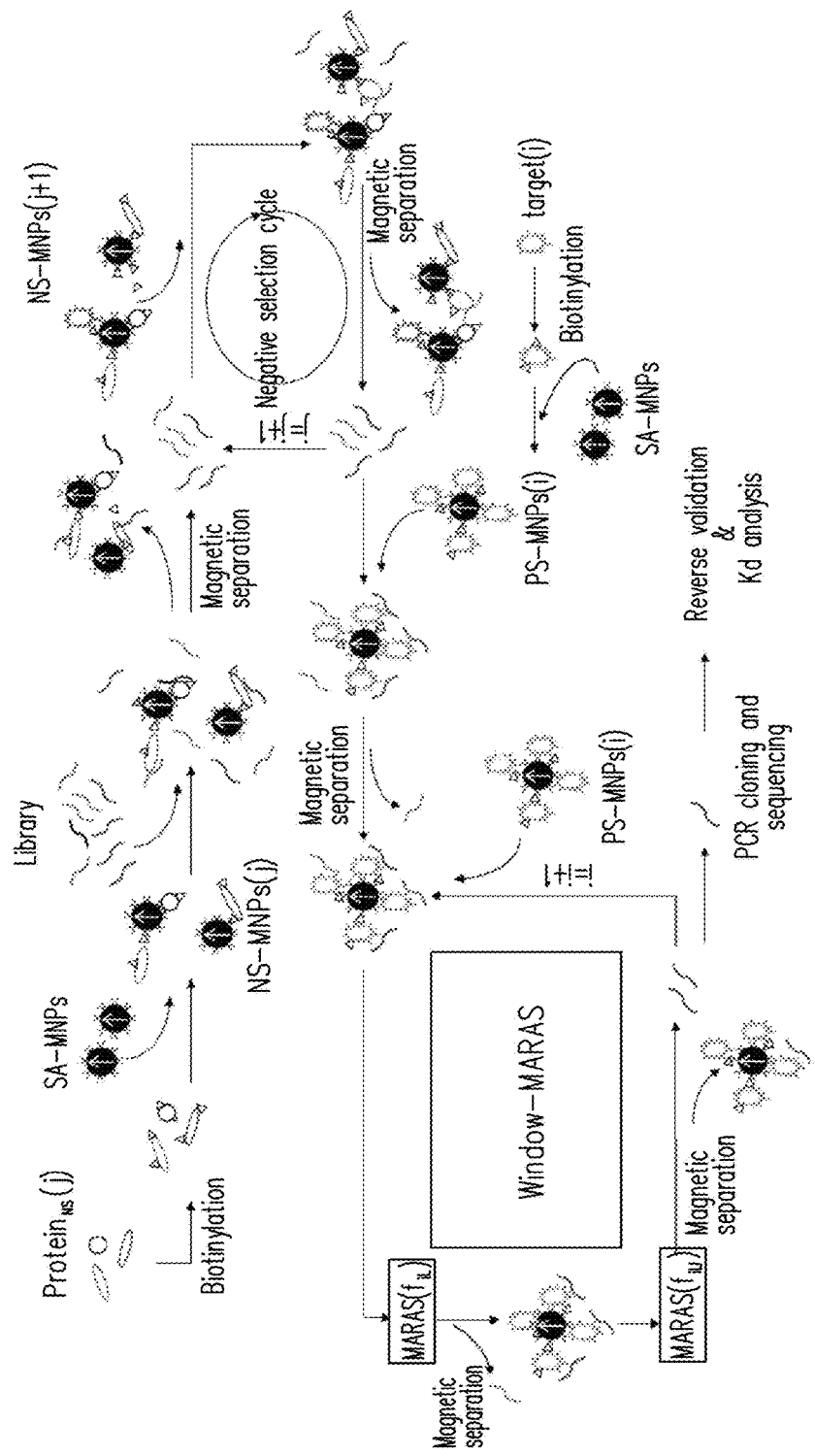
FIG. 2 schematically illustrates the selection method for aptamer capable of conjugating multiple target analytes having differential affinity using window-MARAS method according to some embodiments of the present invention.
Figure 3:
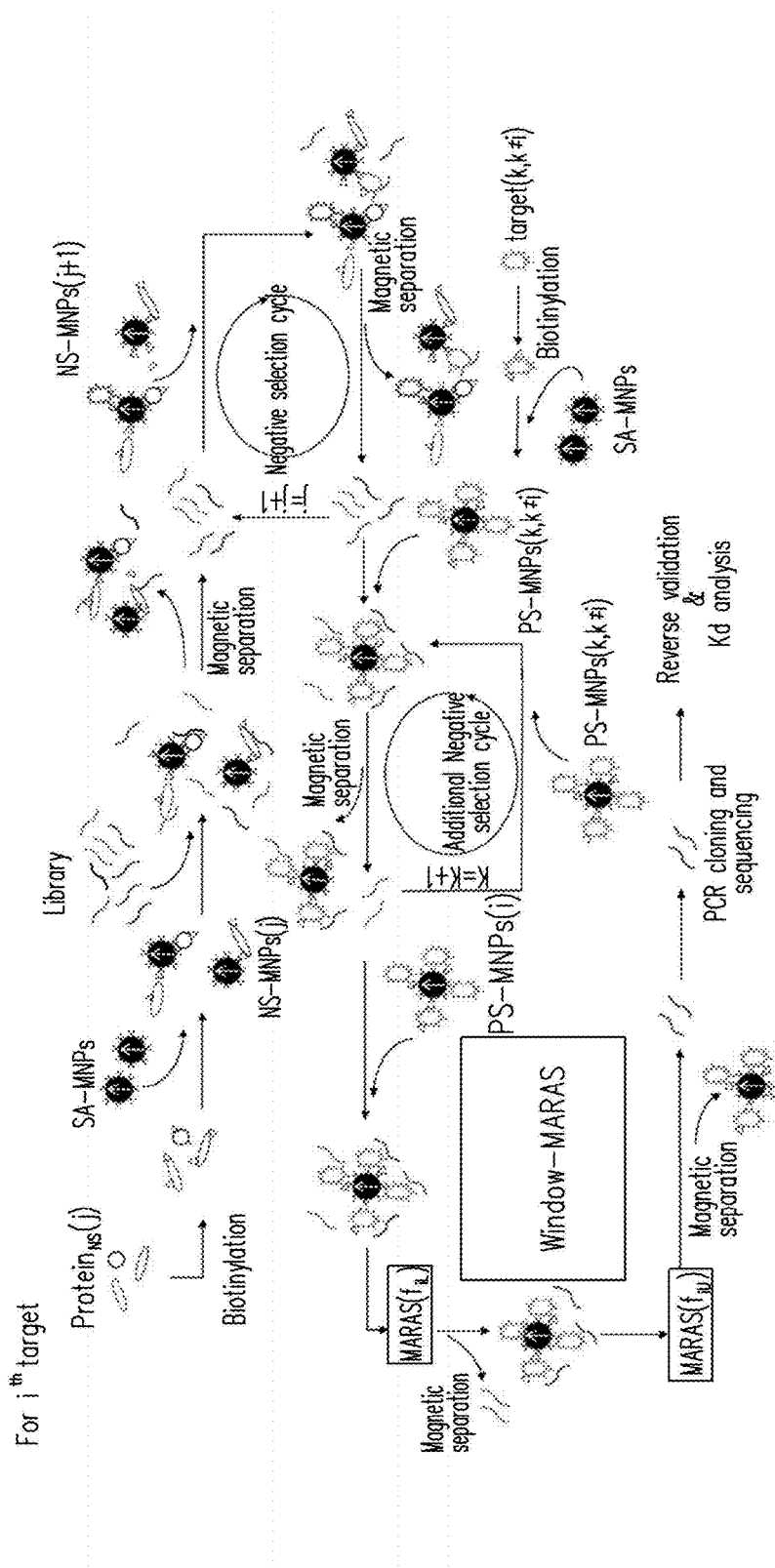
FIG. 3 schematically illustrates the selection method for aptamer capable of conjugating specific target analyte having a desired affinity range using window-MARAS method according to some embodiments of the present invention.

Before the demonstration of multiplex immunoassays, the capture ligands capable of conjugating to multiple target analytes with differential affinities are prepared in order to generate reagents for multiplex immunoassays. In this invention, the aptamers, obtained using window-MARAS, are used as the capture ligands to detect or quantify the target analytes in the immunoassays to demonstrate the feasibility of this invention. The procedure of the selection methods for screening (or generating) aptamers having the characteristics mentioned above are schematically illustrated as shown in FIG. 2 & FIG. 3. In the procedure depicted in FIG. 2 or FIG. 3, four major parts are involved: (1) Material preparation, (2) Negative selection, (3) Positive selection, and (4) Post analyses including PCR amplification, cloning, sequencing, reverse validation, and equilibrium dissociation calculation, and certain process steps or details of four major parts are described below.

In the processes of material preparation, several biological samples (j) (such as human serum samples) pre-treated to remove little or low concentration of interference protein (also called blank sample or blank serum) are individually biotinylated and then conjugated with streptavidin-coated magnetic nanoparticles (SA-MNPs) to form negative-serum magnetic nanoparticles (NS-MNPs$_{(j)}$), and the interference protein may be naturally existing main target analytes in the serum or other analogous proteins. Also, pure main target analytes (i) are individually biotinylated and then conjugated with SA-MNPs to form target-analyte magnetic nanoparticles (PS-MNPs$_{(i)}$). The subscripts j and i of the NS-MNPs and PS-MNPs, respectively, are independently an integer started from 1. It is noted that throughout the embodiments of the aptamer generation and the multiplex immunoassay using aptamer-based reagents, the magnetic particles (MPs) used are not limited to magnetic nanoparticles (MNPs) and the use of magnetic micro particles (MMPs) will achieve similar results in the following experiments similar to those happened in MARAS procedure. The oligonucleotide library includes randomized oligonucleotide sequence with flanked-primers at both ends for PCR amplification. One set of primers, Lab-forward primer and Lab-reverse primer, are used to anneal the degenerating region of the obtained oligonuclcotides (aptamers) during the PCR amplification. The universal T7 primer was used to sequence the nucleotide of the selected aptamer. The entirety of the prior U.S. patent application Ser. No. 14/065,382, filed on Oct. 28, 2013, is hereby incorporated by reference herein and made a part of this specification.

For the negative selection, the oligonucleotide library is incubated with NS-MNPs$_{(1)}$ in binding buffer (BD: 50 mM NaH$_2$PO$_4$, pH 8.0, 150 mM NaCl, 5 mM KCl, 2 mM MgCl$_2$, 0.05% (v/v) Tween-20). After the incubation, a magnetic separation is performed to remove the bound mixture and collect the supernatant containing the remaining oligonucleotides that do not bind with NS-MNPs$_{(1)}$. Then the collected supernatant is incubated with the next NS-MNPs$_{(2)}$ and the processes repeated until the negative selections for all the NS-MNPs$_{(j)}$ are completed. The purpose of multiple negative selection runs is to minimize possibility of binding between selected aptamers and substances other than target analytes in samples in order to reduce possibly false-positive detection during immunoassay application. The same principle can be applied to mono-plex immunoassays for enhancing the detection sensitivity, in which the selected aptamer is only capable of conjugating with single target analyte. Theoretically, the more the negative selection runs are performed the higher the sensitivity (less false-positive detection) can be reached during immunoassays. The final supernatant after the completion of negative selection is collected for the following positive selection. Alternatively, one negative selection run using the mixed NS-MNPs from all NS-MNPs$_{(j)}$ to replace the multiple negative selection runs using individual NS-MNPs$_{(j)}$ will arrive the same result. However, a caution must be taken that using the mixed NS-MNPs the concentration of MNPs in the BD buffer might become too high such that MNPs become easily agglomerate and it has an adverse effect on the selection.

For the positive selection, the collected supernatant from the negative selection is incubated with the PS-MNPs$_{(1)}$ in binding buffer (BD). The magnetic separation is performed to collect the bound mixture and the bound mixture is dispersed in BD buffer, while the unbound oligonucleotides in the supernatant is discarded. The solution is subjected to a window-MARAS at a first rotating magnetic field with a lower-bound frequency, $f_{1L}$, the supernatant is removed by magnetic separation, and the collected bound mixture is re-dispersed in BD buffer. Then a second rotating magnetic field with an upper-bound frequency, $f_{1U}$, is applied to detach the aptamer bound with the first target analyte with a desired affinity. A magnetic separation is performed to remove the bound mixture and collect the supernatant containing the obtained aptamers having desired affinity range toward the first target analyte. Then the supernatant is incubated with the next positive target analyte, PS-MNPs$_{(2)}$, and the procedures are repeated until the positive selections for all the PS-MNPs$_{(i)}$ are completed. The supernatant collected after the completion of the positive selection runs is then used for the following post analyses, such as PCR amplification, cloning, sequencing, reverse validation, and equilibrium dissociation constant calculation. The procedure for generating single aptamer capable of conjugating with multiple target analyses, including the negative and the positive selections, is schematically illustrated in FIG. 2. Alternatively, at the last run of the positive selection, after application of the rotating magnetic field with the lower-bound frequency, the collected bound mixture is re-dispersed, heated, eluted, and magnetically separated to obtain the final supernatant for post analyses. Once the selected aptamer(s) has been verified, it is ready to be used as the capture ligand of reagent(s) for immunoassays or multiplex immunoassays to detect or quantify the quantity of the target analyte(s). This synthesized reagent contains only one kind of aptamer capable of conjugating with multiple target analytes with differential affinities.

It is worthy to be mentioned during the application of rotating magnetic field, the magnetic field strength is kept constant because of the capability of the power amplifier used. However, the field strength can be adjustable. Moreover, for ensuring the obtained aptamer(s) having differential affinity toward different target analytes, a constraint is imposed on the frequency (f) of the applied rotating magnetic fields, i.e., $f_{iL} < f_{iU} \leq f_{(i+1)L}$. Similarly, in the case with the adjustable field strength (H), the constraint becomes $f_{iL} < f_{iU} \leq f_{(i+1)L}$ and/or $H_{iL} < H_{iU} \leq H_{(i+1)L}$. Furthermore, for the same window-MARAS method(s), alternating magnetic fields with a lower-bound and an upper-bound frequency/strength ($f_{iL}$, $H_{iL}$, $f_{iU}$, and $H_{iL}$) can be used to achieve the same results, provided $f_{iL} < f_{iU} \leq f_{(i+1)L}$ and/or $H_{iL} < H_{iU} \leq H_{(i+1)L}$. It is also worthy to be mentioned that if a combined quantity of several target analytes in the samples is the main concern, the same frequency range can be used for these several target analytes during the positive selection.

Alternatively, the reagents containing multiple (different kinds of) aptamers as the capture ligands are to be used for multiplex immunoassays, while each aptamer is able to conjugate with its corresponding target analyte and the binding affinities of different aptamers toward their corresponding target analytes are different (differential affinity). Compared with the procedure outlined in FIG. 2, the procedure illustrated in FIG. 3 is performed with some modification in the parts (2) Negative selection and (3) Positive selection. To generate an aptamer with a desired affinity toward a specific target analyte, these target analytes other than the specific target analyte are deleted from the positive selection runs and added to the negative selection runs. Thus, after the completion of the negative selection runs outlined in FIG. 2, additional negative selection runs are performed using PS-MNPs of the auxiliary target analytes (k) other than the specific main target analyte (i) as NS-MNPs and follows the same procedure of negative selection. For the positive selection, only one run using PS-MNPs of the specific target analyte (i) is needed. The procedure for generating aptamers capable of conjugating a specific target analyte (i) having a desired affinity range is illustrated in FIG. 3. The procedure of FIG. 3 is performed to obtain the corresponding aptamers for all the target analytes. Then all kinds of aptamers, capable of conjugating with their corresponding target analytes, obtained from the procedure can be mixed to form reagents for multiplex immunoassays. It is noted that the constraint for the frequency of rotating magnetic field imposed on FIG. 2, $f_{iL} < f_{iU} \leq f_{(i+1)L}$, should be still applied in order to obtain one kind of aptamer capable of binding to its corresponding target analyte having different affinities as compare to those of different kinds of aptamers toward their corresponding target analytes. Similarly, the constraints mentioned above for the frequency and/or strength of oscillating magnetic fields, the alternative way of negative selection, and the alternative way of the last run of the positive selection are still applicable. Moreover, it is worthy to be noted that the positive selection run(s) can be performed prior to the negative selection runs for the procedures outlined in FIG. 2 and FIG. 3 to arrive the same results similar to that of a standard MARAS procedure.

Figure 4:
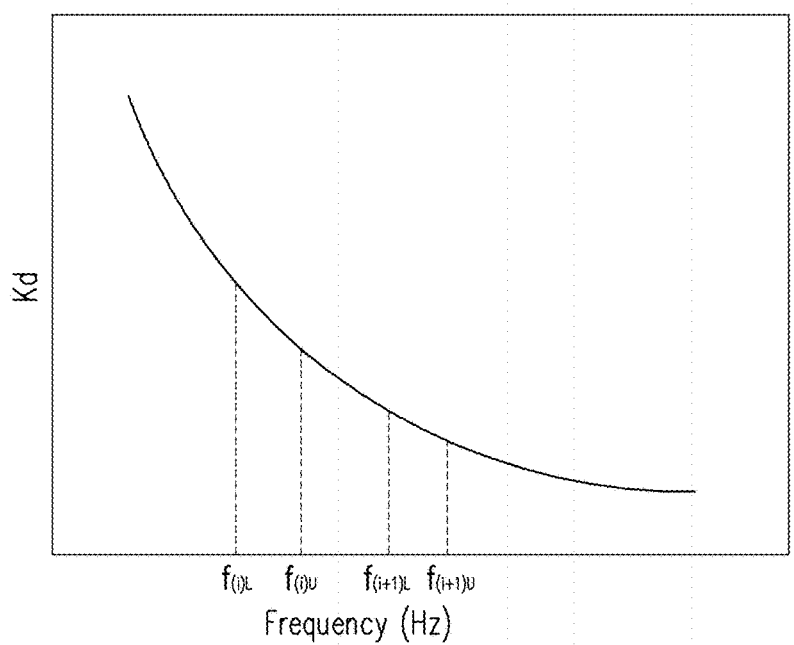
FIG. 4 schematically illustrates the frequency dependency using window-MARAS for screening the aptamers with various dissociation constants (differential affinity) according to some embodiments of the present invention.

In FIG. 4, the relationship of the magnetic field frequency applied in MARAS and dissociation constants (Kd) of the aptamers screened by MARAS is conceptually shown and aptamers having a desirable range of binding affinity (or a desirable Kd value or range) can be selected by applying a lower-bound frequency and an upper-bound frequency. By varying the lower-bound frequency ($f_{(i)L}$) and the upper-bound frequency ($f_{(i)U}$) of the applied oscillating magnetic field without overlapping the frequency range, aptamers having differential affinities toward target analytes can be obtained.

Experimental Setting of MARAS

Figure 5A:
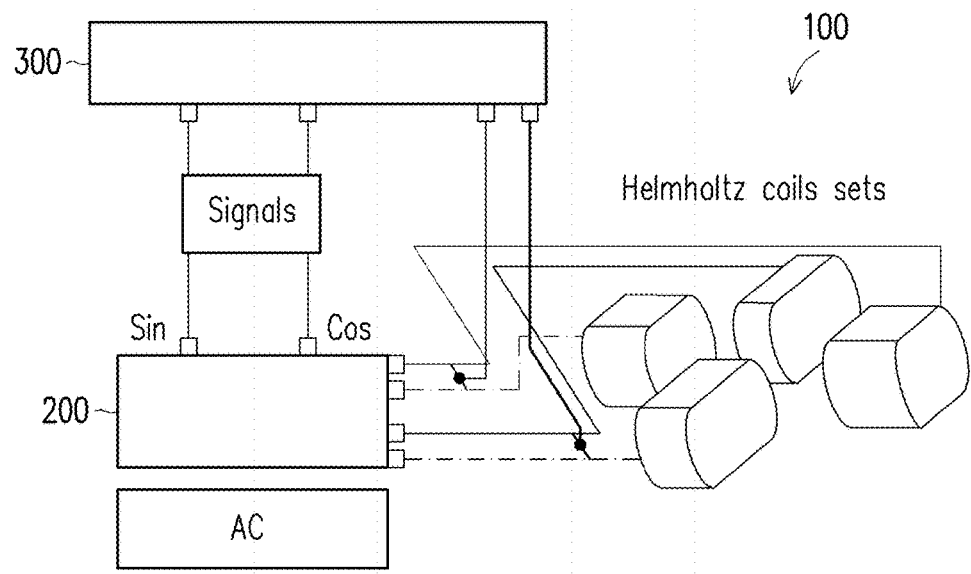
FIG. 5A is a schematic diagram of the experimental setting for the rotating magnetic field magnetic-assisted rapid aptamer selection (RO-MARAS) method according to one embodiment of the present invention.
Figure 5B:
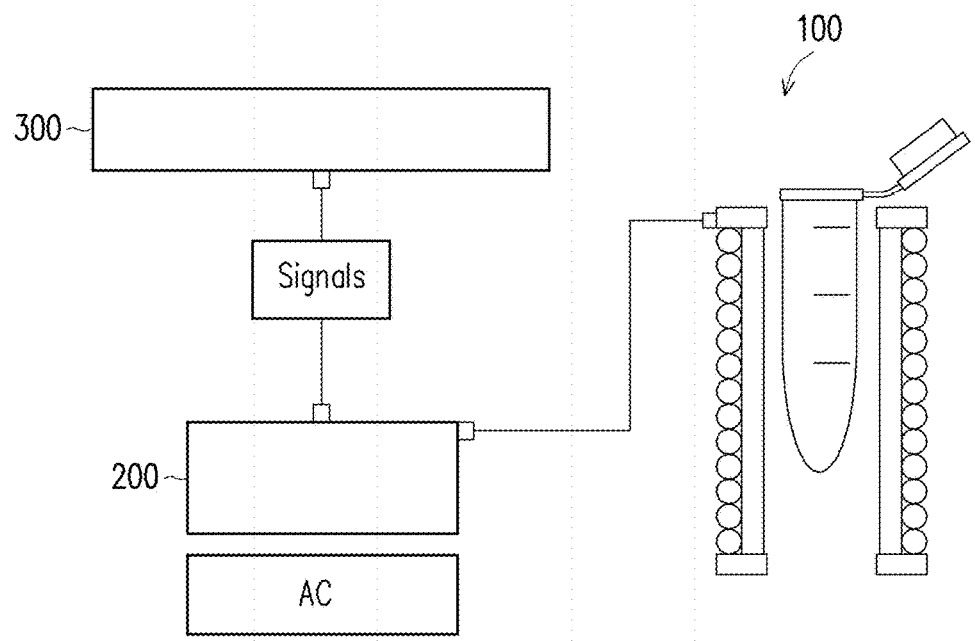
FIG. 5B is a schematic diagram of the experimental setting for the alternating magnetic field magnetic-assisted rapid aptamer selection (AC-MARAS) method according to one embodiment of the present invention.
Figure 6A:
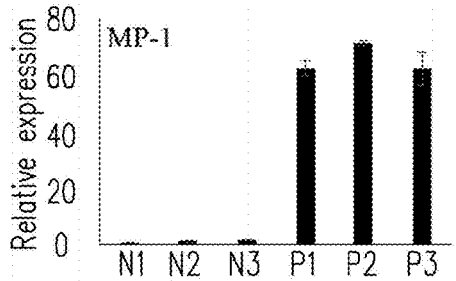
FIG. 6A-6F show the results of reverse validation of obtained six multiplex binding-aptamers via quantitative real-time PCR (q-PCR) according to some embodiments of the present invention.
Figure 6B:
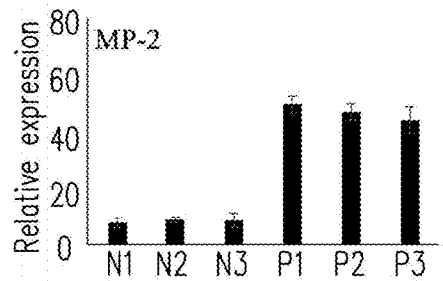
Figure 6C:
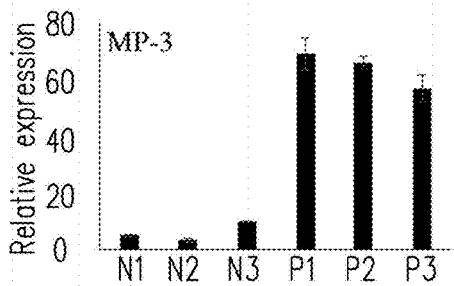
Figure 6D:
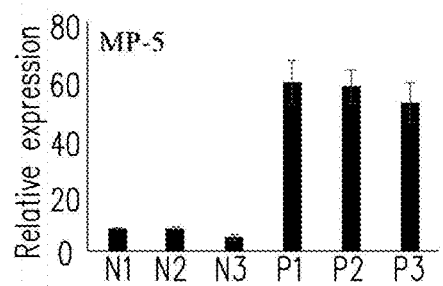
Figure 6E:
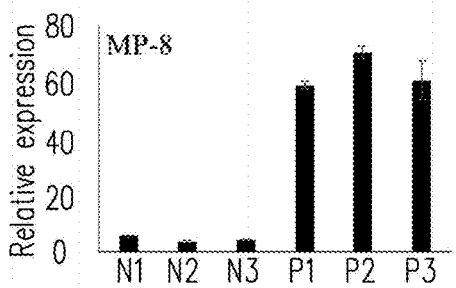
Figure 6F:
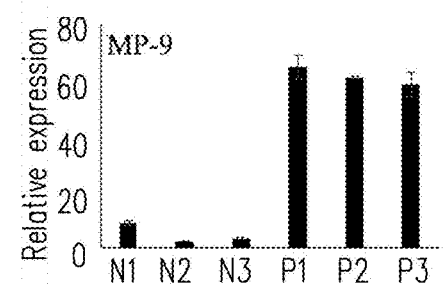
Figure 7A:
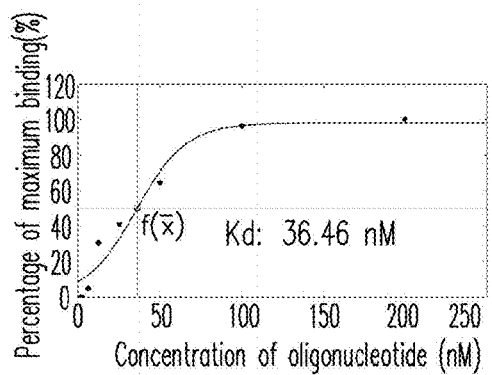
FIG. 7A-7F show the equilibrium dissociation constants (Kd) of the MP-1 aptamer toward multiple target analytes according to some embodiments of the present invention.
Figure 7B:
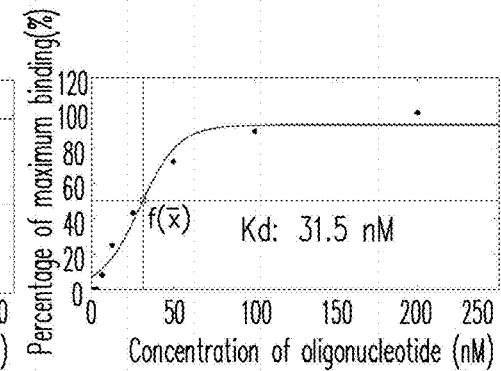
Figure 7C:
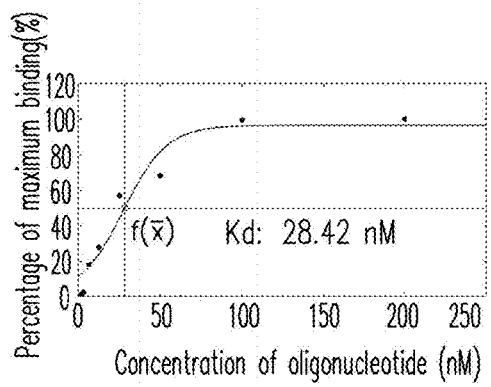
Figure 7D:
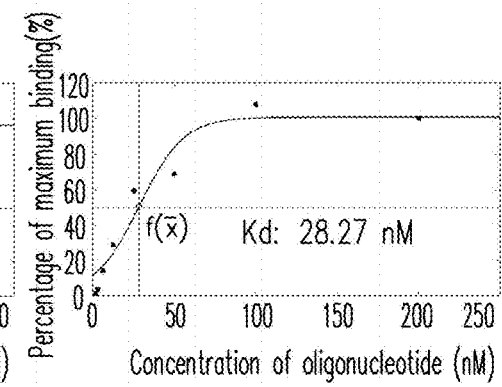
Figure 7E:
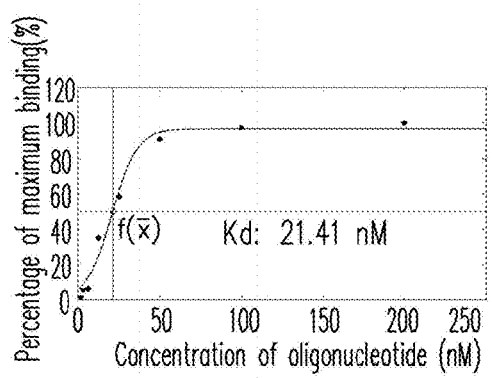
Figure 7F:
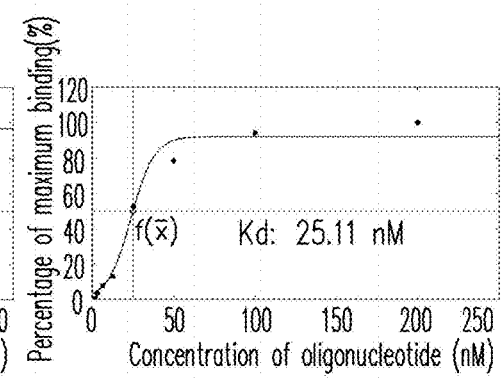

The experimental setting for performing MARAS method was described as below. The experimental setting includes at least two sets of coils 100 for generating an oscillation magnetic field, a power amplifier 200, a signal generator 300 and is operated with the LABVIEW computer program. The oscillation magnetic fields used in MARAS may be either a rotating magnetic field as in the case of rotating magnetic field-MARAS (RO-MARAS) or an alternating magnetic field as in the case of alternating magnetic field-MARAS (AC-MARAS). For RO-MARAS, the rotating magnetic field was generated by two sets of Helmholtz coils 100 placed orthogonally. The LABVIEW program 300, via a NI BNC-2110 capture box, was used to send two signals, cos(ωt) and sin(ωt), into a two-channel power amplifier 200 (HCA3030D). These two signals were then amplified equally, which drove two sets of coils simultaneously to produce a rotating magnetic field. The experimental setting is schematically shown in FIG. 5A. In the figures, the sample was placed at the intersection of the central lines of two sets of Helmholtz coils 100. However, other alternative setting may also be used to generate the rotating magnetic field. For AC-MARAS, the magnetic field was generated by a single excitation solenoid 100 driven by a signal generator 300 and current generator unit 200, as schematically shown in FIG. 5B, in which the sample was placed inside the solenoid 100. It is noted that the setting of FIG. 5A can also be used for AC-MARAS if the computer program send only one signal to one set of Helmholtz coil to generate the AC magnetic field. Furthermore, other alternative setting may also be used to generate the alternating magnetic field. Moreover, other types of oscillation magnetic field may be also applicable, such as an elliptical magnetic field which can be generated by using different amplification factors of the power amplifier 200 for the sine and cosine signals from the signal generator 300 using the setup depicted in FIG. 5A.

In exemplary embodiments, the capture ligands are ssDNA aptamers and the target analytes are proteins. Firstly, one exemplary embodiment demonstrates the method for selecting a class of single ssDNA aptamer (one kind), from a randomized oligonucleotide library, capable of binding to three different target analytes having differential affinities. The obtained ssDNA aptamer acts as the capture ligands in a reagent to detect and quantify these three specific target analytes for multiplex immunoassay. Yet, using the same three target analytes of above, another exemplary embodiment demonstrates the method for selecting three classes of ssDNA aptamers (three kinds) capable of binding to its corresponding target analyte, individually, having different desired affinity range; by mixing the obtained aptamers to form a reagent that is able to detect and quantify these target analytes for multiplex immunoassays. Moreover, using the reagents and target analytes of above, other exemplary embodiments use quantitative real-time PCR (q-PCR) experiments to demonstrate the applicability of multiplex immunoassay utilizing the differential affinity.

Material Preparation

Before performing the window-MARAS methods, it is required to prepare the materials. The material preparation includes preparing the random oligonucleotide library, preparing the target analytes and incubating the target analytes with the random oligonucleotide library. These preparation steps will be summarized in the following sections.

Oligonucleotide Library and Primers

The length of initially oligonucleotide library is 50-mer and consists of a randomized 20-mer midsection (N20) and two primers with 15-mer fixed section at both ends. The oligonucleotide sequence is (SEQ ID NO:1) 5'-AGCAG-CACAGAGGTC-N20- (SEQ ID NO:2) GCGTGCTAC-CGTGAA-3', synthesized and PAGE purified by MDBio (MDBio, Taipei, Taiwan). One set of primers, (Lab-F: 5'-AGCAGCACAGAGGTC-3' (SEQ ID NO:1) and the Lab-R: 5'-TTCACGGTAGCACGC-3' (SEQ ID NO:3)), was used to anneal the 5' and 3' degenerating region of the library during the PCR amplification. 5'-biotin labeled primers, Lab-biotin-F and Lab-biotin-R, with the same sequence as described above, are used to isolate the biotin-forward single strand and forward single strand nucleotides from the double strand PCR product, respectively. The universal T7 primer was used to sequence the nucleotide of the selected aptamer (T7: 5'-TAATACGACTCACTATAGGG-3' (SEQ ID NO:4)). It is mentioned that different lengths and sequences of random oligonucleotide library and their corresponding primers can be used without altering the results of this invention.

CRP, HBs Ag, HCV NS3 and Serum Coated, Bio-Functionalized Magnetic Particles

In this study, human C-reactive protein (CRP), hepatitis B surface antigen (HBs Ag), and hepatitis C virus nonstructural protein 3 (HCV NS3) were purchased from MyBioSource (MyBioSource, San Diego USA) and used as the binding target-1 (P1), -2 (P2), and -3 (P3), respectively, for the positive selections. Six healthy volunteers provided serums for three negative selections and three blind tests. The CRP, HBs Ag and HCV NS3 protein concentration of volunteer's serums were undetectable (CRP concentration, <0.02 μg/ml, Beckman DxC analyzer, Beckman Corporation, Fullerton, Calif., HBV DNA undetectable, <15 IU/ml, q-PCR, HCV DNA undetectable, <15 IU/ml, q-PCR). Even though the CRP content may be under the detection limit, CRP still exists in the serums. Therefore, in order to avoid the interference during the aptamer selection stage and the validation stage, the CRP present in all serums were removed prior to the experiments (blank serums). A 200 μl of each healthy human serum was incubated with overdose latex particles which consist of a polystyrene core and a hydrophilic shell covalently binding with anti-CRP monoclonal antibodies (Siemens Health-care Diagnostics, Eschbom, Germany). CRP presented in the serums formed antigen-antibody complexes with latex particles. After centrifugation (10,000 rpm, 5 minutes), the CRP present in the serums was removed and the supernatant was collected carefully. Three healthy human serums were named as negative serum-1, -2, and -3 and the other three were named as blind serum-1, -2, and -3. It is noted that if directly using serums with low concentration of interference protein(s) (also called minimal-interfering serums) as negative samples for negative selections, the results of this invention will be the same, except the efficacy of selecting suitable aptamers will be reduced due to the removal of some possible candidate oligonucleotides bound to the interfering protein(s) during negative selections. The magnetic nanoparticles were bio-functionalized by coating streptavidin on the outermost surface of magnetic nanoparticles (SA-MNPs) and were dispersed in PBS (pH=7.4) to form SA-MNP reagent and were purchased from Magqu (Magqu, Taipei, Taiwan). The average hydrodynamic diameter of SA-MNPs in the reagent was 50 nm. The reagent had a concentration of SA-MNPs with 0.3 emu/g. The biotinylation kit (EZ-Link Sulfo-NHS-Biotinylation Kit) was purchased from Pierce (Rockford, Ill., USA). A 200 μg of pure CRP, HBs Ag, and HCV NS3 proteins (for positive selection), three negative serums (for negative selection, -1, -2, and -3), and three blind serums (for blind test, -1, -2, and -3) were biotinylated, according to the manufacturer's instructions. Then all the biotinylated molecules (positive proteins, negative serums, and blind serums) were individually incubated with 50 µl of SA-MNP reagent. The high-affinity binding between the streptavidin and biotin ensures the conjugation between the magnetic nanoparticles (MNPs) and biotinylated target analytes (CRP, HBs Ag, and HCV NS3), biotinylated substances in negative serums (negative serum-1, -2, and -3) and blind serums (blind serum-1, -2, and -3). The prepared biofunctionalized magnetic nanoparticle reagents included reagents containing CRP-MNPs (P1), HBs Ag-MNPs (P2), and HCV NS3-MNPs (P3) for positive selection; negative serum-1 MNPs (N1), negative serum-2 MNPs (N2), and negative serum-3 MNPs (N3) for negative selection; blind serum-1 MNPs (B1), blind serum-2 MNPs (B2), and blind serum-3 MNPs (B3) for blind test. If needed, the positive, negative serum, or blind serum MNPs were obtained from the corresponding positive, negative serum or blind serum reagents, respectively, by magnetic separation. The collected positive, negative serum or blind serum MNPs were washed 3 times with BD buffer and finally collected using a magnetic stand.

Example 1: Procedure for Generating Aptamer Having Different Desired Binding Affinity Range Toward Different Target Analytes The schematic procedure for generating aptamers having different desired binding affinity ranges toward multiple target analytes by window-MARAS is depicted in FIG. 2 and the detailed process steps of the Example 1 are described. A randomized oligonucleotide library was provided as the starting library. 100 µM library dissolved in BD buffer and diluted to 10 µl with BD buffer in a micro-tube, heated to 95° C. for 5 minutes, then snap cooled at 4° C. for the formation of secondary structures and stayed at room temperature for 30 minutes. First, the negative selection was performed by incubating the library with negative serum-1 MNPs (N1), obtained by magnetic separation from 5 µl of negative serum-1 MNP reagent, for 30 minutes at room temperature. After magnetic separation, oligonucleotides bound with negative serum-1 MNPs were removed. The collected supernatant was then incubated with negative serum-2 MNPs (N2) and negative serum-3 MNPs (N3) and magnetically separated to remove the bound mixture, sequentially. The final supernatant was collected for the following positive selection. The positive selection was described as following: CRP-MNPs (P1), obtained by magnetic separation from 5 µl of CRP-MNP reagent, was added into the micro-tube containing the final supernatant from the negative selection and incubated for 30 minutes at room temperature. The unbound oligonucleotides were removed with a magnetic stand and the bound mixture was washed twice with 1 ml of BD buffer. A 100 µl of BD buffer was added to re-disperse the bound mixture in the micro-tube and the micro-tube was placed in the RO-MARAS setup. The strength of the rotating magnetic field used through the experiments was 14 gauss. The bound mixture solution was then first subjected to a lower-bound rotating magnetic field of frequency $f_{1L}$=15 KHz for 10 minutes at room temperature. In order to avoid agglomeration due to the action of the magnetic field on the magnetic nanoparticles, the bound mixture solution was stirred by pipetting every 2.5 minutes, which was also applied for the following window-MARAS procedures. A magnetic separation was performed to remove detached oligonucleotides in the supernatant and 100 µl BD buffer was added to re-disperse the bound mixture. The bound mixture solution was then subjected to window-MARAS under an upper-bound rotating magnetic field of frequency $f_{1U}$=20 KHz for 10 minutes at room temperature. Another magnetic separation was performed to collect supernatant, which containing aptamers could bind to CRP protein selected under the frequency range, 15 KHz≤f≤20 KHz. The HBs Ag-MNPs (P2), obtained by magnetic separation from 5 µl of HBs Ag-MNP reagent, was added into the micro-tube containing the collected supernatant and incubated for 30 minutes at room temperature. After removing unbound oligonucleotides by magnetic separation and washing, 100 µl BD buffer was added to re-disperse the bound mixture. The bound mixture solution was subjected to the next lower-bound rotating magnetic field of frequency $f_{2L}$=20 KHz for 10 minutes at room temperature. A magnetic separation was performed to remove detached oligonucleotides in the supernatant and 100 µl BD buffer was added to re-disperse the bound mixture. The bound mixture solution was subjected to window-MARAS under the next upper-bound rotating magnetic field of frequency $f_{2U}$=27 KHz for 10 minutes at room temperature. A magnetic separation was performed to collect supernatant, which containing aptamers could bind to CRP and HBs Ag proteins and were selected under frequency ranges 15 KHz≤f≤20 KHz and 20 KHz≤f≤27 KHz, respectively. The HCV NS3-MNPs (P3), obtained by magnetic separation from 5 µl of HCV NS3-MNP reagent, was added into the micro-tube containing the collected supernatant and incubated for 30 minutes at room temperature. After wash and magnetic separation to remove unbound oligonucleotides, 100 µl BD buffer was added to re-disperse the bound mixture. The bound mixture solution was subjected to window-MARAS under the final lower-bound rotating magnetic field of frequency $f_{3L}$=27 KHz for 10 minutes at room temperature. A magnetic separation was performed to remove supernatant and the bound mixture was retained. The retained bound oligonucleotides in the mixture were eluted from the HCV NS3-MNPs by heated to 95° C. for 5 min in 100 µl BD buffer. A magnetic separation was performed to collect the supernatant containing the multiplex binding aptamers (MP-aptamer) capable of binding with CRP, HBs Ag and HCV NS3 proteins, selected under frequency ranges 15 KHz≤f≤20 KHz, 20 KHz≤f≤27 KHz, and 27 KHz≤f, respectively. During the heating process, HCV NS3 protein was also detached from magnetic particles. Then a purification step was taken to remove HCV NS3 protein from the supernatant by using DNA Extraction Miniprep System (Viogene, Taipei, Taiwan) and the obtained aptamers were eluted in 20 µl ddH$_2$O. It is worthy to be mentioned that in order to assay multiple target analytes utilizing aptamers with differential affinity, the constraint, $f_{1L}<f_{1U}=f_{2L}<f_{2U}=f_{3L}$, on the frequency of the applied rotating magnetic field are applied.

Example 2: Procedure for Generating Aptamers for Corresponding Target Analytes with Different Binding Affinities The schematic procedure for generating aptamers binding to different target analytes having different desired binding affinity for multiple target analytes by window-MARAS is described in the FIG. 3. Certain detailed process steps similar to the steps described in Example 1 or FIG. 2 will not be repeated herein. Multiple runs of the negative selection were performed and the purpose of multiple negative selection is to minimize the nonspecific binding and to reduce the possibility of false positive results for diagnoses. As shown in FIG. 3, before starting the positive selection for the first target analyte CRP-MNPs (P1), additional negative selections were performed to ensure the obtained aptamer binding only to the specific positive target analyte (first target analyte) but not to other target analytes. The other target analytes for additional negative selection including: HBs Ag-MNPs (P2) and HCV NS3-MNPs (P3) were served as extra negative target analytes. The collected supernatant from negative selection runs was incubated with HBs Ag-MNPs (P2), obtained by magnetic separation from 5 μl of HBs Ag-MNP reagent, for 30 minutes at room temperature and magnetically separated to remove the bound mixture. The collected supernatant was then incubated with HCV NS3-MNPs (P3), obtained by magnetic separation from 5 μl of HCV NS3-MNP reagent, for 30 minutes at room temperature. After magnetic separation, oligonucleotides bound with extra target analytes including: HBs Ag-MNPs (P2) and HCV NS3-MNPs (P3) were removed and the supernatant was collected for the positive selection. The positive selection was described as following: CRP-MNPs (P1), obtained by magnetic separation from 5 μl of CRP-MNP reagent, was added into the micro-tube containing the final supernatant from the additional negative selections and incubated for 30 minutes at room temperature. The unbound oligonucleotides were removed with a magnetic stand and the bound mixture was washed twice with 1 ml of BD buffer. A 100 μl of BD buffer was added to re-disperse the bound mixture in the micro-tube and the micro-tube was placed in the RO-MARAS setup. The strength of the rotating magnetic field used throughout the experiments is 14 gauss. The bound mixture solution was first subjected to a lower-bound rotating magnetic field of frequency $f_{1L}$=15 KHz for 10 minutes at room temperature. In order to avoid agglomeration due to the action of the magnetic field on the magnetic nanoparticles, the bound mixture solution was stirred by pipetting every 2.5 minutes, which was also applied for the following window-MARAS procedures. A magnetic separation was performed to remove detached oligonucleotides in the supernatant and 100 μl BD buffer was added to re-disperse the bound mixture. The bound mixture solution was then subjected to window-MARAS under an upper-bound rotating magnetic field of frequency $f_{1U}$=20 KHz for 10 minutes at room temperature. Another magnetic separation was performed to collect supernatant, which containing aptamer could bind only to CRP protein selected under the frequency range, 15 KHz≤f≤20 KHz (K1 aptamer). The generating process of aptamer binding to HBs Ag-MNPs (P2) was same as describe above, and used CRP-MNPs (P1) and HCV NS3-MNPs (P3) as extra negative target analytes. The lower-bound rotating magnetic field of frequency $f_{2L}$=20 KHz and upper-bound rotating magnetic field of frequency $f_{2U}$=27 KHz were used. The obtained aptamer could only bind to HBs Ag protein selected under the frequency range, 20 KHz≤f≤27 KHz (K2 aptamer). Finally, the same process was repeated for generating aptamer which could bind to HCV NS3-MNPs (P3) using CRP-MNPs (P1) and HBs Ag-MNPs (P2) as extra negative target analytes. The lower-bound frequency of the rotating magnetic field is $f_{3L}$=27 KHz. After applying the lower-bound magnetic field, a magnetic separation was performed to remove the detached oligonucleotides. The retained bound oligonucleotides in the mixture were eluted from the HCV NS3-MNPs by heated to 95° C. for 5 minutes in 100 μl BD buffer. A magnetic separation was performed to collect the supernatant containing the HCV NS3 binding aptamers (K3 aptamer). The three collected supernatants contained the aptamers (K1, K2, and K3 aptamers) capable of binding to CRP, HBs Ag, and HCV NS3 selected under frequency ranges 15 KHz≤f≤20 KHz, 20 KHz≤f≤27 KHz, and 27 KHz≤f, respectively. The last supernatant also contained HCV NS3 protein which was detached from magnetic particles due to the heating process. Then a purification step was taken to remove HCV NS3 protein from the supernatant by using DNA Extraction Miniprep System and the obtained aptamers were eluted in 100 μl BD buffer. It is worthy to be mentioned that in order to assay multiple target analytes utilizing aptamers with differential affinity, the constraint, $f_{1L}<f_{1U}=f_{2L}<f_{2U}=f_{3L}$, on the frequency of the applied rotating magnetic field are applied.

As discussed above, DNA aptamers are oligonucleotides that bind to a specific target analyte, and from the oligonucleotide library (large random sequence pool). The aptamers selected by the aforementioned window-MARAS selection method(s) are subjected to post analyses, such as PCR amplification, cloning, sequencing and binding affinity calculation (in terms of dissociation constants).

PCR Amplification, Cloning and Sequencing Analysis of Selected Aptamers

The supernatants which were collected from each window-MARAS experiments were precipitated with 1 ml of 100% cold alcohol and diluted by 100 μl ddH$_2$O for a following PCR amplification. The collected supernatants were subsequently amplified by PCR with Lab-F and Lab-R primers. The PCR reaction which contained 1.25 U of DNA polymerase (Invitrogen), 0.1 mM dNTPs, 0.5 mM MgSO$_4$, 0.5 nM primers, was performed under the following conditions: 5 minutes at 95° C.; 35 cycles of 40 seconds at 95° C., 40 seconds at 60° C., 40 seconds at 72° C.; and 10 minutes at 72° C. The PCR product was purified by using a DNA Extraction Miniprep System. The purified product was subcloned into a pGEM-T Easy vector (Promega, Madison, Wis., USA). The cloning procedure was performed according to the manufacturer's instruction. The plasmids of picked up colonies were purified by using a High-Speed Plasmid Mini Kit (Geneaid, Taipei, Taiwan). The plasmids were sequenced by using an Applied Biosystems PRISM 3730 DNA automatic sequencer and a Big Dye terminator cycle sequencing kit (Foster City, Calif., USA).

For the Selected Aptamers in Example 1

Reverse Validation of Selected MP-Aptamers

Six aptamers (MP-aptamers) were used to validate the selection method following the selection procedure as shown in FIG. 2. For each plasmid picked from the cloning experiments, 10 ng of aptamer clone plasmid was used as a PCR template to generate double strand DNA (dsDNA) of MP-aptamer with Lab-biotin-R and Lab-F primers. The PCR condition and procedure were as described above. After the completion of PCR amplification, the PCR product was mixed with SA-MNPs, obtained by magnetic separation from 5 μl of SA-MNP reagent. The forward single strand MP-aptamer (nonbiotinylated strand) was separated from the immobilized complementary strand, by being incubated with 0.15 N of fresh NaOH for 5 min. The bound SA-MNPs were removed with a magnetic stand. An equal amount of 0.15 N of HCl was added to the collected supernatant to adjust the final pH to 7.0, after which the forward ssDNA MP-aptamer was precipitated with 1 ml of 100% ice-cold alcohol. The concentration of the single strand MP-aptamer was determined with a NanoDrop 2000c spectrophotometer (Thermo Fisher Scientific, Wilmington, Del., USA). A 100 nM of the MP-aptamer in 20 μl of BD buffer was heated to 95° C. for five minutes and cooled at 4° C. for the formation of secondary structures. The MP-aptamer solutions were incubated with CRP-MNPs (P1), HBs Ag-MNPs (P2), HCV NS3-MNPs (P3) and negative serum-MNPs (N1, N2, and N3), individually, for 30 minutes at room temperature, of which the protein MNPs were obtained from 5 µl of corresponding reagents via magnetic separation. A magnetic separation was performed to collect the bound mixtures. The collected bound mixture was washed twice by BD buffer and re-dispersed in 20 µl of BD buffer. Another magnetic separation was performed to remove the supernatant and collect the bound mixture. The bound mixture was re-dispersed in 100 µl ddH$_2$O and heated to 95° C. for 5 minutes to elute aptamers from the MNPs for CRP-MNPs (P1), HBs Ag-MNPs (P2), HCV NS3-MNPs (P3) and negative serum-MNPs (N1, N2, and N3). A magnetic separation was performed to remove the MNPs and collect the supernatant. The amount of the aptamers which eluted from the MNPs in the supernatant was measured by a SYBR based q-PCR in duplicate. The mixture for each q-PCR run was 10 µl containing 2 µl of nucleic acids, 2.5 µl of SYBR Green PCR master mix (Applied Biosystems) and 0.5 nM of primers. The reaction condition was as follows: 95° C. for 3 minutes; 40 cycles at 94° C. for 30 seconds; 60° C. for 30 seconds; and 72° C. for 30 seconds. The primers, Lab-F and Lab-R, were used for q-PCR to amplify the nucleic acids.

There are six multiplex binding aptamers (MP-aptamers), MP-1, MP-2, MP-3, MP-5, MP-8, and MP-9 which were isolated by window-MARAS and the sequences of the 20N regions of the MP-aptamers screened by window-MARAS were listed in the Table 1. The validation of the aptamer selection method following the procedure of FIG. 2 was performed by reversely targeting the positive controls (CRP, HBs Ag, and HCV NS3-MNPs) and negative controls (serum-1, -2, and -3 MNPs). The results were shown in the FIG. 6A-6F. The levels of binding toward the positive controls were much higher than those of negative controls. As expected, the MP-aptamer(s) only bound with the target analytes but not to other molecules presented in the serums. These results demonstrate the success of the MP-aptamer selection procedure. The MP-1 aptamer was selected and used for further analyses.

TABLE 1

The sequences of 20N region of the MP-aptamers screened by window-MARAS

| Aptamer clone name | Target sequence |
|---|---|
| MP-1 (SEQ ID NO: 5) | CTGCATCACGAAGCCTGGCA |
| MP-2 (SEQ ID NO: 6) | AGGTCCTCCGAATGGGACTA |
| MP-3 (SEQ ID NO: 7) | CCGGAACACCAGAAGCACGT |
| MP-5 (SEQ ID NO: 8) | CCCGTCACCTATTTTTCCGT |
| MP-8 (SEQ ID NO: 9) | ACAGGGGAAGAAGCGTCACC |
| MP-9 (SEQ ID NO: 10) | CCTTGGCATGATTGTCTCCT |

Determination of Equilibrium Dissociation Constants by q-PCR

The affinity of the MP-aptamers toward the CRP, HBs Ag, and HCV NS3 target analytes was described by the equilibrium dissociation constant (Kd), which was measured by a q-PCR, separately. The single strand MP-aptamers were generated as described above. For each target analyte, a series of progressively diluted MP-aptamers (200 nM to 1.5625 nM) in 20 µl of BD buffer were heated to 95° C. for 5 minutes and cooled at 4° C. for the formation of secondary structures. Partial diluted MP-aptamers were retained as an input control (input). For Target 1, CRP-MNPs (P1), obtained from washing and magnetically separating 5 µl of CRP-MNP (P1) reagent, were added into each of microtubes containing diluted MP-aptamers and incubated for 30 minutes at room temperature. A magnetic separation was performed to collect the bound mixture. The bound mixture were washed twice with 100 µl of BD buffer. The bound MP-aptamers were eluted from the CRP-MNPs by heating the bound mixture at 94° C. for 10 minutes in 20 µl of ddH$_2$O. The CRP-MNPs in the solution were removed with a magnetic stand, and the supernatants were collected. Both the input control and eluted MP-aptamers were precipitated with 1 ml of 100% ice-cold alcohol. The input control and eluted MP-aptamers were individually dissolved in test tubes filled with 100 µl of ddH$_2$O. The quantities of the MP-aptamers in each test tube, including input control tube and eluted MP-aptamer tubes, were calculated by q-PCR. The q-PCR was performed with MicroAmp optical 96-well reaction plates, and the threshold cycle (ct) value was calculated automatically using the maximum correlation coefficient approach with StepOnePlus Real-Time PCR Systems software, version 2.0 (Applied Biosystems). The mixture for each q-PCR run was 10 µl containing 2 µl of nucleic acids, 2.5 µl of SYBR Green PCR master mix (Applied Biosystems) and 0.5 nM of primer Lab forward and Lab reverse. The reaction condition was as follows: 95° C. for 3 minutes; 40 cycles at 94° C. for 30 seconds; 60° C. for 30 seconds; and 72° C. for 30 seconds. The concentrations of the MP-aptamers in the input control and the eluted MP-aptamers were calculated, using a 200 nM concentration of MP-aptamers as indicative of maximum binding. The Kd value of the selected MP-aptamer was then determined by fitting a saturation binding curve based on the experimental data via a curve fitting program, CurveExpert1.3 (curveexpert.webhop.net). The Kd value of the selected MP-aptamer was performed in duplicate for each q-PCR run and was expressed as the mean±standard deviation from three separate experiments performed. The same procedure were repeated for Target 2 and Target 3, HBs Ag-MNPs (P2) and HCV NS3-MNPs (P3), to determine the Kds of MP-aptamers.

The representative fitting curves and the calculated results of dissociation constants were shown in FIG. 7A-7F. FIG. 7A-7F shows the equilibrium dissociation constants of MP-1 aptamer toward multiple target analytes; the target analytes are respectively CRP in FIG. 7A-7B, HBs Ag in FIGS. 7C-7D, and HCV NS3 protein in FIG. 7E-7F. The result shows that the value of Kd of MP-1 aptamer is 33.98±3.5 nM for CRP, 28.34±0.1 nM for HBs Ag, and 23.26±2.62 nM for HCV NS3. The results indicate that the selected MP-1 aptamer is capable of binding with three different target analytes and can be used for multiplex immunoassays. The values of the dissociation constant of MP-1 aptamer is decreasing with Target 1, Target 2, and Target 3, sequentially. These results are consistent with our previous results that the aptamer generated by MARAS platform was dependent on the frequency and strength of magnetic field condition and the higher the magnetic field frequency was applied the lower the dissociation constant was obtained. The sequential decrease of the dissociation constant of MP-1 aptamer toward various target analytes is attributed to the enhancement of competitive mechanism induced by the increase of magnetic field frequency at a constant field strength for these three target analytes during screening process.

Verification of the Aptamer Binding by Enzyme-Linked Immunosorbent Assay (ELISA)

An aptamer-based ELISA was performed as below to verify the binding of MP-aptamer. Biotinylated MP-aptamer was synthesized and purchased from MDBio. 10 nM biotinylated MP-aptamers in each micro-tube containing 20 µl of BD buffer were heated to 95° C. for 5 minutes and cooled at 4° C. for the formation of secondary structures. CRP-MNPs (P1), HBs Ag-MNPs (P2), and HCV NS3-MNPs (P3), obtained from 5 µl of corresponding reagent by magnetic separation, were incubated with 10 nM biotinylated MP-aptamer in micro-tubes for 30 minutes at room temperature, separately. After washing and performing magnetic separation to remove unbound oligonucleotides, 100 µl BD buffer was added to re-disperse the bound mixture. The bound mixture solution was subjected to a rotating magnetic field of frequency (15 KHz), for 10 minutes at room temperature. A magnetic separation was performed to remove detached oligonucleotides in the supernatant and named as "<15 KHz" fraction. 100 µl BD buffer was added to re-disperse the bound mixture. The following process was performed with 20 KHz and 27 KHz, sequentially. All detached corresponding oligonucleotide fractions were collected and named as "15-20 KHz" and "20-27 KHz". Finally, 100 µl BD buffer was added to re-disperse the bound mixture and heated to 95° C. for 5 minutes to elute the aptamers from target MNPs. A magnetic separation was performed to collected the supernatant and named as ">27 KHz". Each set of collected supernatants included "<15 KHz", "15-20 KHz", "20-27 KHz", and ">27 KHz" fractions for all three target analytes. The collected supernatants were incubated with 100 µl of streptavidin-HRP (Sigma-Aldrich, Mo., USA) in micro-tubes for 1 hour at room temperature. CRP-MNPs (P1), HBs Ag-MNPs (P2), and HCV NS3-MNPs (P3), obtained from 1 µl of CRP-MNP, HBs Ag-MNP, and HCV NS3-MNP reagents by magnetic separation, respectively, were added into these three sets of micro-tubes, separately, and incubated for one hour at room temperature. The bound mixture in the micro-tube was retained by magnetic separation and washed 3 times with 200 µl BD buffer. The color was developed by adding 100 µl 3,3',5,5'-tetramethyl-benzidine (TMB, Sigma-Aldrich) substrate solution and by having the mixture stand at room temperature for 5 minutes. The reaction was terminated with an addition of 100 µl of 2N HCl, and the absorbance was measured in duplicate at 405 nm by using EMax precision microplate reader (Molecular Devices, CA, USA).

The results are shown in FIG. 8A-8D with the duplicate photo images and the corresponding optical intensity from assaying the CRP, HBs Ag, and HCV NS3 under different magnetic field conditions. FIG. 8A-8C show the duplicate photo images (upper and lower rows) for the validation of MP-1 aptamer capable of conjugating multiple target analytes with differential affinity by aptamer-based ELISA, whereas the target analytes are in FIG. 8A: CRP (P1), in FIG. 8B: HBs Ag (P2), and in FIG. 8C: HCV NS3 (P3). FIG. 8D shows the measured optical density of control (<15 KHz), P1 (15-20 KHz), P2 (20-27 KHz), and P3 (>27 KHz). MP-1 aptamer could bind with CRP-MNPs, HBs Ag-MNPs, and HCV NS3-MNPs. MP-1 aptamer bound with CRP-MNPs but detached under magnetic field of frequency 20 KHz and strength 14 gauss. Furthermore, the MP-1 aptamer bound to HBs Ag-MNPs under the magnetic field condition with strength of 14 gauss and frequency range up to 27 KHz. Finally, the MP-1 aptamer still bound to HCV NS3-MNPs under magnetic field of frequency 27 KHz and strength 14 gauss. It is noted that the magnetic field conditions used here are the same as those during the selection stage. The result reveals that the binding affinity between the MP-1 aptamer and the different target analytes was depended on the window-MARAS condition. In other words, one can alter window-MARAS conditions during selection stage to obtain aptamers with the different desired affinity toward target analyte(s) and the obtained aptamer is capable of binding to multiple target analytes with differential affinity. By utilizing this specific future, an aptamer-based multiplex immunoassay utilizing differential affinity becomes feasible.

Establishment of Standard Calibration Curve by q-PCR

Standard calibration curves were individually determined by using a serial dilution of CRP-MNPs, HBs Ag-MNPs, and HCV NS3-MNPs, obtained from 1 µl of CRP-MNP (Target 1), HBs Ag-MNP (Target 2), and HCV NS3-MNP (Target 3) reagents by magnetic separation, respectively, in 10 µl BD buffer. The corresponding target quantities in the diluted solution are 4000, 2000, 1000 . . . , and finally 31.25 ng. 1 µM MP-aptamer dispersed in 10 µl BD buffer was heated to 95° C. for 5 minutes and cooled at 4° C. for the formation of secondary structures. Target MNPs (Target 1, 2, and 3), obtained from each diluted solution by magnetic separation, were added into each BD buffer containing MP-aptamer and incubated for 30 minutes at room temperature. The bound mixture was collected and the supernatant was removed by magnetic stand. The bound aptamers were eluted from the MNPs by heating at 94° C. for 10 minutes in final volume 100 µl of ddH$_2$O. The supernatant was collected and the MNPs were removed by magnetic separation. The amount of eluted oligonucleotides in each collected supernatant was analyzed by q-PCR. The q-PCR analyses were performed in duplicate as described before. The PCR cycle number (expressed as relative expression level), at which the fluorescence intensity reaches a set cycle threshold value (ct), versus target quantities was calculate by $2^{-ct}$. The standard curve was linearly fitted from sixteen experimental data points. A best fit method was used to calculate the $R^2$ value and obtain the linear equation. The standard calibration curve(s) can be used in determining the quantities of target analytes in samples for the future analyses.

Figure 9A:
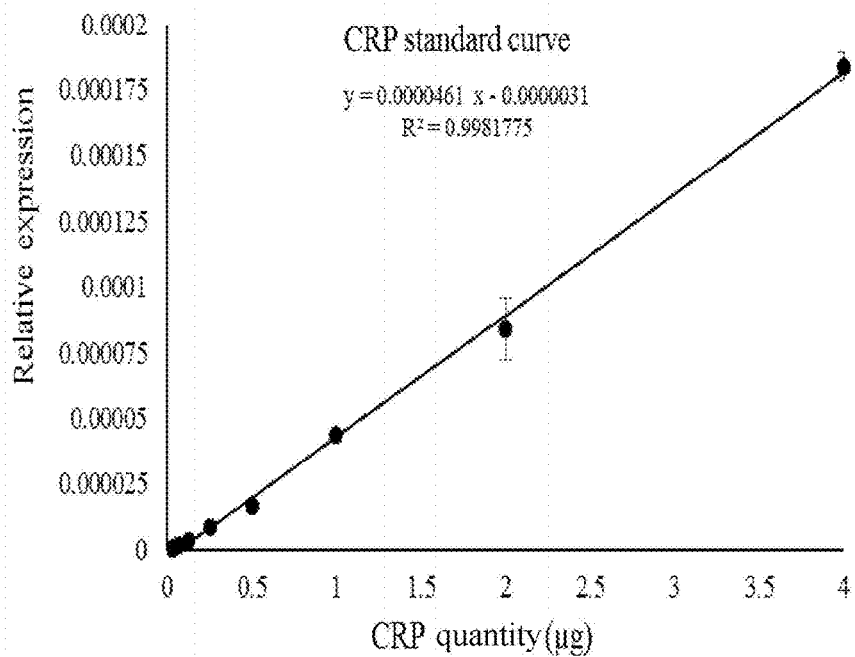
FIG. 9A-9C show the standard calibration curve for target analytes using the MP-1 aptamer as a capture ligand by q-PCR, the relative expression level vs. CRP, HBs Ag, and HCV NS3 quantities in BD buffer, respectively.
Figure 9B:
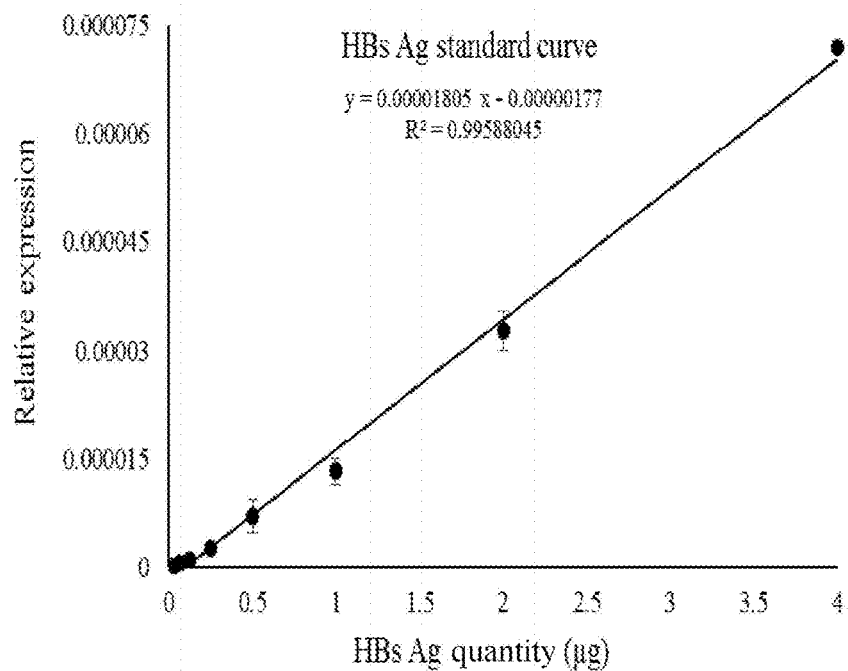
Figure 9C:
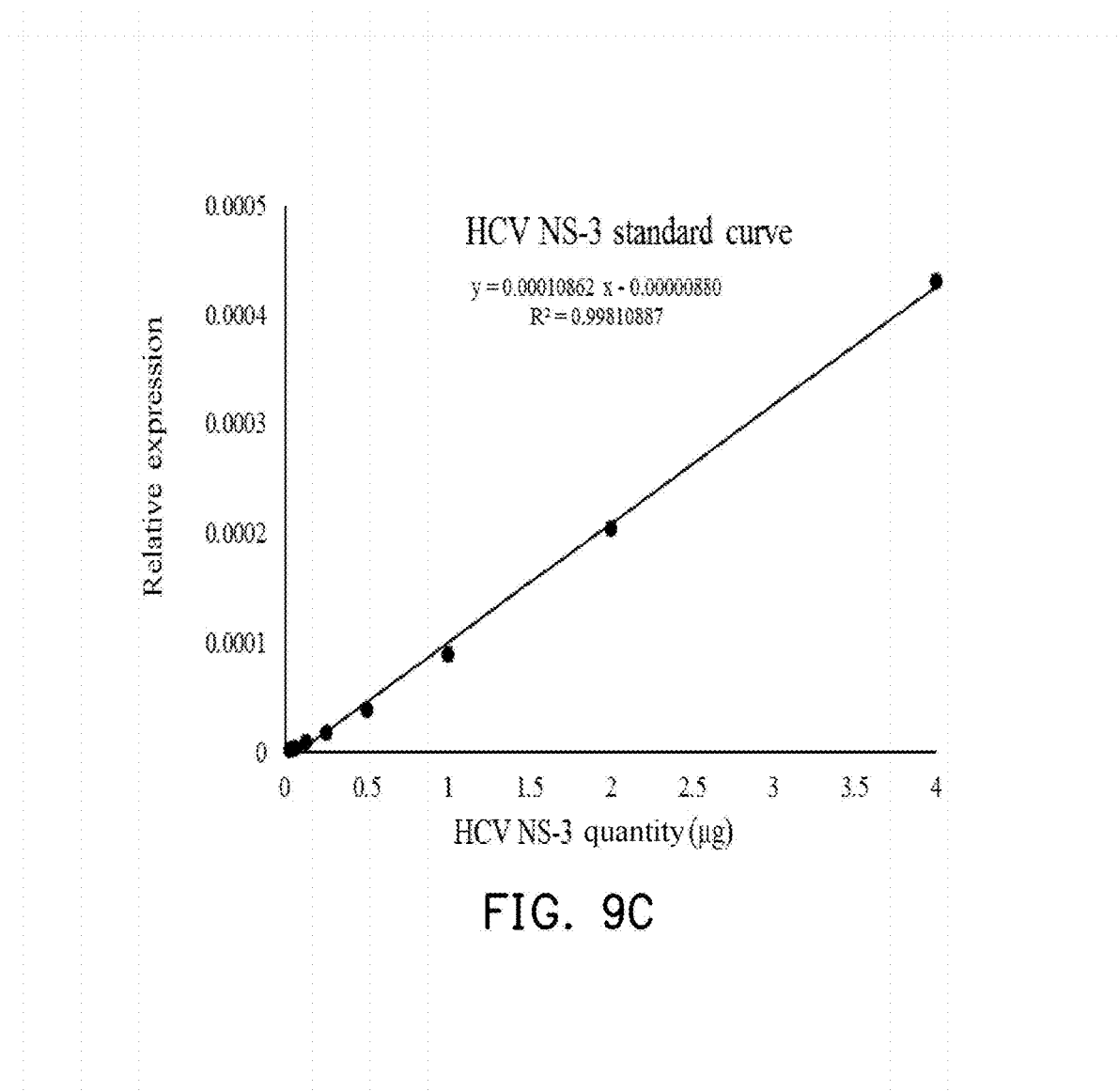

FIG. 9A-9C show the standard calibration curves of MP-1 aptamer for CRP, HBs Ag, and HCV NS3, respectively. As expected, the relative expression levels are linearly proportional to the quantity of the target analytes in the samples. The result reveals that the dynamic range of the measurement depends on the amount of MP-aptamer presented in the reagent during immunoassays.

Determination of Recovery Rate Using MP-1 Aptamer in Assaying Human Serums

Three volunteer's blind serums were used as blind samples for the determination of recovery rate of MP-aptamer as a capture ligand, of which CRP, HBs Ag, and HCV NS3 concentrations were undetectable, named as: blind serum-1 (B1), -2 (B2), and -3 (B3). The preparation of blind serum MNPs is as described in material section. Mixture of pure protein of equal quantity (1.6 gig protein each) of CRP, HBs Ag, and HCV NS3 MNPs, obtained from 0.4 µl of corresponding MNP reagent by magnetic separation, was spiked into 40 µl BD buffer in micro-tubes. One quarter of the mixture solution (10 µl) was used as a control and named as "Targets in BD buffer". The remaining mixture solution was equally divided into three parts (10 µl each), of which each part was individually spiked with blind serum MNPs, obtained from 0.1 µl of blind serum MNP reagent by magnetic separation, and named as "Targets in Serum-1", "Targets in Serum-2", and "Targets in Serum-3", corresponding to blind serum-1 (B1), -2 (B2), and -3 (B3), respectively. For the recovery rate experiment of "Targets in BD buffer", a 5000 nM MP-aptamer in 20 µl of BD buffer in a micro-tube was heated to 95° C. for five minutes and cooled at 4° C. for the formation of secondary structures and then the protein MNPs, obtained from the "Targets in BD buffer" by magnetic separation, were added into the micro-tube for 30 minutes at room temperature. The supernatant in the micro-tube was removed by magnetic stand and the bound mixture was collected and dispersed in 100 µl BD buffer. The bound mixture solution was placed inside RO-MARAS platform and under an initial window-MARAS condition with field frequency of 15 KHz for 10 minutes at room temperature. A magnetic separation was performed to remove the supernatant and 100 µl BD buffer was added to disperse the retained bound mixture. The bound mixture solution was subjected to a second window-MARAS condition with field frequency of 20 KHz for 10 minutes at room temperature. A magnetic separation was performed to collect the supernatant and named as "15-20 KHz". A 100 µl BD buffer was added to disperse the retained bound mixture. The bound mixture solution was subjected to the third window-MARAS condition with frequency of 27 KHz for 10 minutes at room temperature. A magnetic separation was performed to collect the supernatant and named as "20-27 KHz". A 100 µl BD buffer was added to disperse the retained bound mixture. The bound mixture solution was heated at 94° C. for 10 minutes to elute aptamers from the MNPs. A magnetic separation was performed to collect the supernatant and named as ">27 KHz". All the collected supernatants, "15-20 KHz", "20-27 KHz", and ">27 KHz", were precipitated with 1 ml of 100% ice-cold alcohol and individually dissolved in test tubes filled with 100 µl of ddH$_2$O. The amount of oligonucleotides in each test tube was analyzed by q-PCR in duplicate as described before and calculated via the corresponding linear equation of the standard calibration curves to determine the CRP, HBs Ag, and HCV NS3 quantities in "Targets in BD buffer" sample. The same procedure was repeated for "Targets in Serum-1", "Targets in Serum-2", and "Targets in Serum-3".

Figure 10:
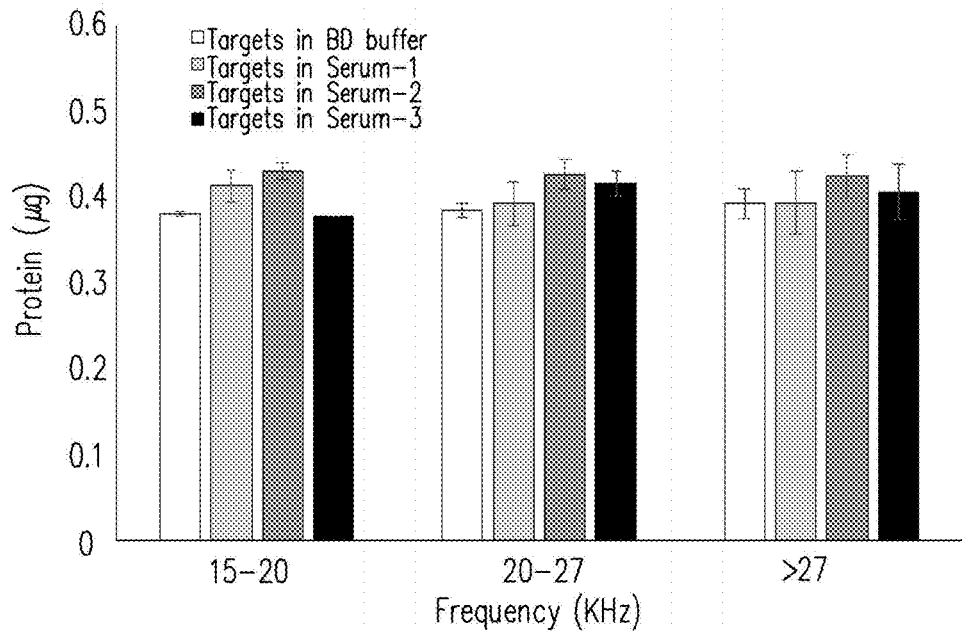
FIG. 10 shows the recovered quantities of target analytes in samples using the reagent containing MP-1 aptamer as the capture ligand according to some embodiments of the present invention.

The result of the recovered quantities of target analytes using MP-1 aptamer as capture ligands was shown in FIG. 10. The recovery rates of target analytes were calculated based on the quantity of spiked target analytes, which was 0.4 µg each ideally, and were between 107.59% and 94.39%. There is no significant difference between the measured target analyte quantities in BD buffer, blind serum-1, -2, and -3. The protein recovered quantity was similar under different magnetic frequency range. It is noted that theoretically the levels of recovered target analytes in serums should be equal or higher than that in BD buffer due to nonspecific binding as proteins presented in serums other than target analytes and the deviation can be attributed to the experimental error magnified by q-PCR. However, by comparing the results with or without the blind human serums, it reveals that there is a limited interference from proteins in the blind serums other than target proteins. This result clearly illustrates that the MP-1 aptamer could specific bind to Target 1, 2, and 3 in BD buffer and human serums, and can be used for multiplex immunoassay to detect the concentration of CRP, HBs Ag, and HCV NS3 proteins in a single assay.

Figure 11:
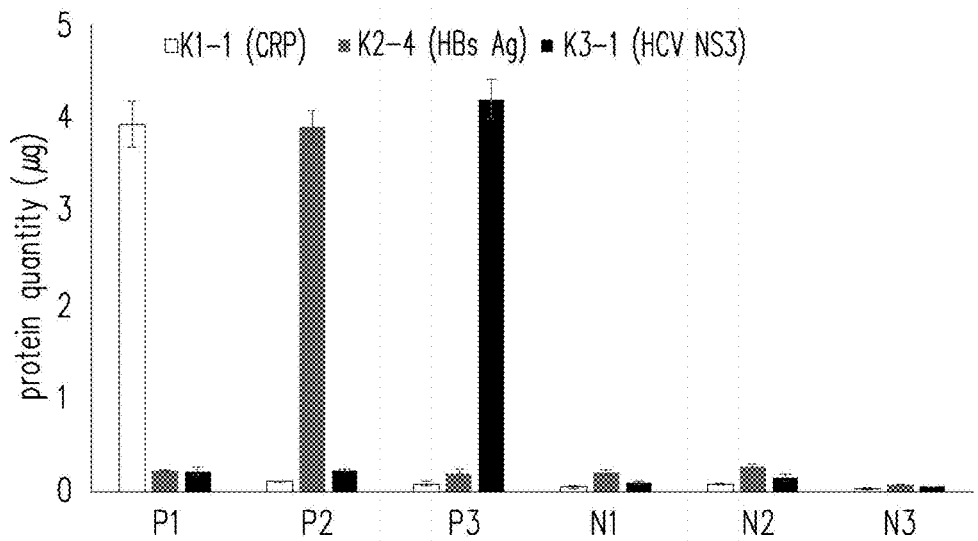
FIG. 11 shows the results of reverse validation of obtained aptamers via q-PCR according to some embodiments of the present invention.

For the Selected Aptamers in Example 2
Reverse Validation of Selected Aptamers
There are eight aptamers binding for CRP protein, five aptamers binding for HBs Ag protein, and two aptamers binding for HCV NS3 proteins were selected and generated by the selection method of Example 2 following the procedure as shown in FIG. 3. Aptamers (K1-1 for CRP, K2-4 for HBs Ag, and K3-1 for HCV NS3) were representatively used to validate the selection method following the procedure as shown in FIG. 3, and these aptamers were selected based on their low cross-reaction as demonstrated later. The forward single strand aptamers (non-biotinylated strand), including K1-1, K2-4, and K3-1 aptamers, were generated using the same procedure outlined in Example 1 ([0059]). A 5000 nM of the K1-1 aptamers in 120 µl of BD buffer was heated to 95° C. for five minutes and cooled at 4° C. for the formation of secondary structures. An equal amount (20 µl) of K1-1 aptamer solution was separately incubated with CRP-MNPs (P1), HBs Ag-MNPs (P2), HCV NS3-MNPs (P3), and negative serum-MNPs (N1, N2 or N3), for 30 minutes at room temperature. The protein MNPs were obtained from 1 µl of corresponding reagents by magnetic separation. A magnetic separation was performed to collect the bound mixtures. The collected bound mixture was washed twice by BD buffer and re-dispersed in 20 µl of BD buffer. Another magnetic separation was performed to remove the supernatant and collect the bound mixture. The bound mixture was re-dispersed in 100 µl ddH$_2$O and heated to 95° C. for 5 minutes to elute aptamers from the protein MNPs for CRP-MNPs (P1), HBs Ag-MNPs (P2), HCV NS3-MNPs (P3), and negative serum-MNPs (N1, N2, and N3). A magnetic separation was performed to remove the MNPs and collect the supernatant. The amount of the aptamers which eluted from the MNPs in the supernatant was measured by SYBR based q-PCR analysis in duplicate. The mixture for each q-PCR run was 10 µl containing 2 µl of nucleic acids, 2.5 µl of SYBR Green PCR master mix (Applied Biosystems) and 0.5 nM of primers. The reaction condition was as follows: 95° C. for 3 minutes; 40 cycles at 94° C. for 30 seconds; 60° C. for 30 seconds; and 72° C. for 30 seconds. The primers, Lab-F and Lab-R, were used for q-PCR to amplify the nucleic acids. The results of q-PCR (expressed as the relative expression level) indicated the binding between K1-1 and the samples, CRP-MNPs (P1), HBs Ag-MNPs (P2), HCV NS3-MNPs (P3), and negative serum-MNPs (N1, N2, and N3). The same procedure was repeated for K2-4 and K3-1 aptamers. FIG. 11 shows the results of reverse validation of obtained aptamers K1-1, K2-4, and K3-1 via q-PCR. The levels of binding toward the corresponding positive controls were much higher than those of positive controls other than the specific one and negative controls which are at noise level. For example, the K1-1 aptamer only bound with CRP but not bound to the other positive controls (HBs Ag and HCV NS3) and negative controls (serum-1, -2, and -3). Similar results were also obtained for K2-4 and K3-1 aptamers.

Cross-Reaction Investigation of Selected Aptamers
Cross-reaction experiments were performed to examine the interaction between aptamers. The cross-reaction investigation of selected aptamers was described as below. Aptamers (K1-1 for CRP, K2-4 for HBs Ag, and K3-1 for HCV NS3) were used to representatively demonstrate the cross-reaction investigation, which were selected based on their low cross-reaction. The investigation included three separate experiments, that is, the interactions of K1-1 vs. K2-4, K1-1 vs. K3-1, and K2-4 vs. K3-1. In each experiment, the solution containing aptamer (aptamer-1) without biotinylation was prepared and equally divided: the first half was used as the input control and the second half was mixed and incubated with equal quantity of another biotinylated aptamer (aptamer-2). In the second half, a portion of aptamer-1 would associate with aptamer-2 due to hybridization. After incubation with SA-MNPs, the aptamer mixture was subjected to a magnetic separation to remove this portion. The collected supernatant contained aptamer-1 which did not hybridize with aptamer-2. The amount of the remaining aptamer-1 in the supernatant was compared to that in the input control by q-PCR. The difference between them indicated the level of interaction between aptamer-1 and aptamer-2. Wherein, the aptamer-1 (nonbiotinylated aptamer) was generated as described before; for the biotinylated aptamers (aptamer-2), the bound SA-MNPs including the bound immobilized complementary strand, generated by the same procedure as described in [0059] of Example 1, were collected with the magnetic stand. A 20 μl BD buffer was added to disperse the SA-MNP bound mixture. The SA-MNP bound mixture solution was heated at 70° C. for 1 second. Then, magnetic separation was performed to collect the supernatant, which contained biotinylated aptamers. Here, K1-1 and K2-4 aptamers were representatively used to illustrate the cross-reaction experiment which was described below. For the cross-reaction experiment of K1-1 and K2-4 aptamers, 10 nM of K1-1 and biotinylated K2-4 aptamers were individually heated to 95° C. for five minutes in 10 μl BD buffer and cooled at 4° C. for the formation of secondary structures. The K1-1 aptamers (non-biotinylated aptamer) were incubated with the biotinylated K2-4 aptamers for 30 minutes at room temperature. The mixture was then mixed and incubated with SA-MNPs, obtained from 5 μl of SA-MNP reagent by magnetic separation. Biotinylated K2-4 aptamers would bind to SA-MNPs due to the biotin-streptavidin interaction. Due to hybridization, a portion of non-biotinylated K1-1 aptamers would associate with biotinylated K2-4 aptamers. A magnetic separation was performed to remove the bound SA-MNPs and the supernatant was precipitated with 1 ml of 100% ice-cold alcohol and dissolved in a test tube filled with 100 μl of ddH$_2$O. The amount of oligonucleotides in the test tube was analyzed by q-PCR analysis in duplicate as described before. The same process was performed for the investigation of the cross-reaction between K1-1 vs. K3-1 aptamers, and K2-4 vs. K3-1 aptamers.

Figure 12:
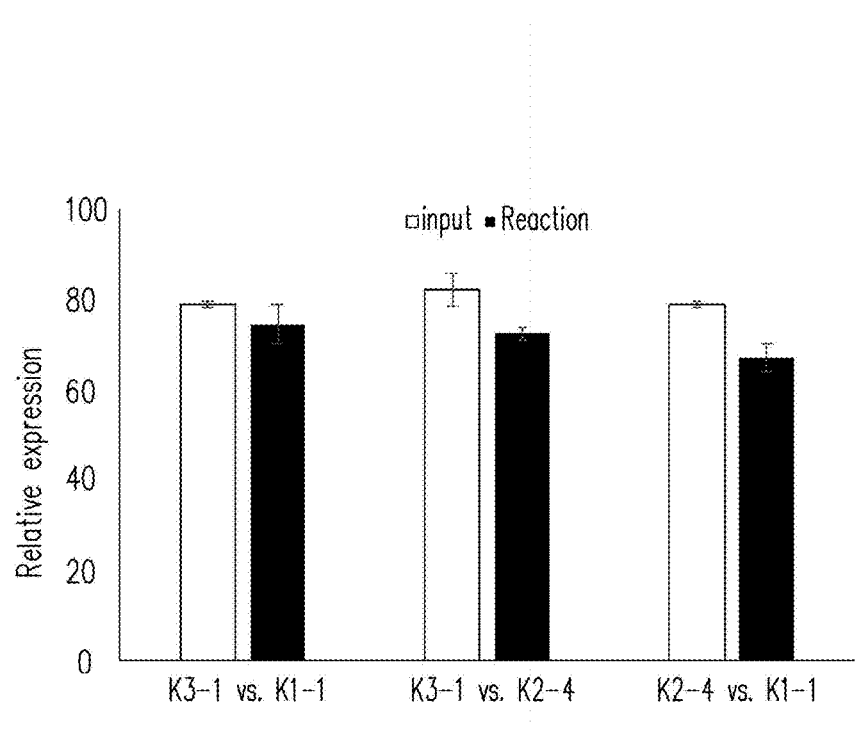
FIG. 12 shows the experimental results of cross-reaction experiments of obtained aptamers via q-PCR according to some embodiments of the present invention.
Figure 13A:
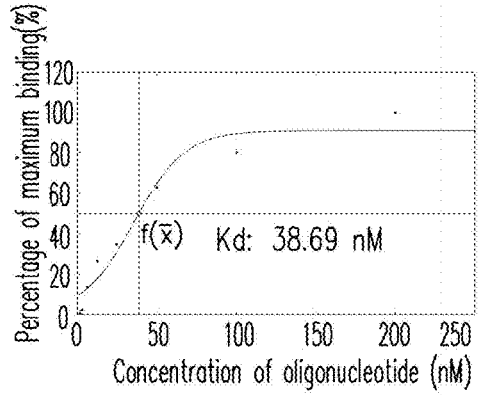
FIG. 13A-13F show the equilibrium dissociation constants of Aptamer K1-1, K2-4, and K3-1 toward different target analytes according to some embodiments of the present invention.
Figure 13B:
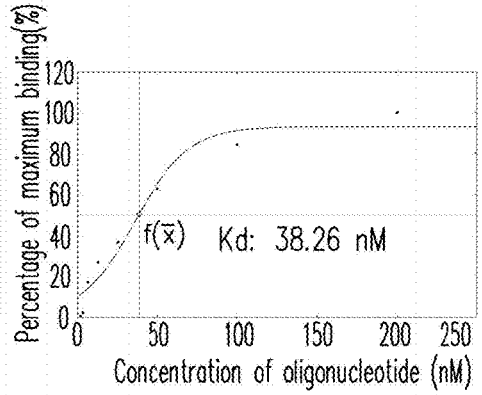
Figure 13C:
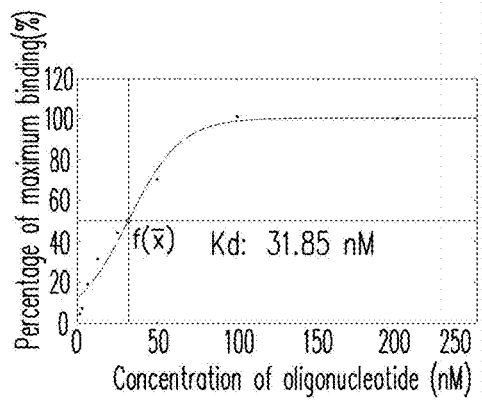
Figure 13D:
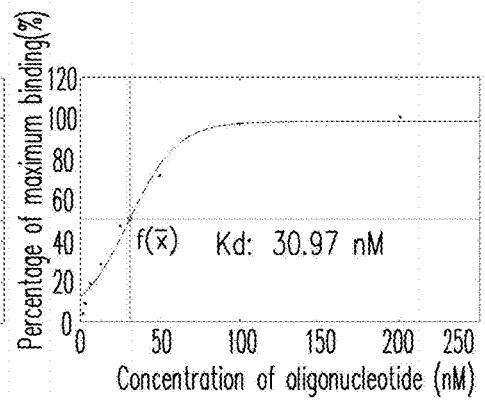
Figure 13E:
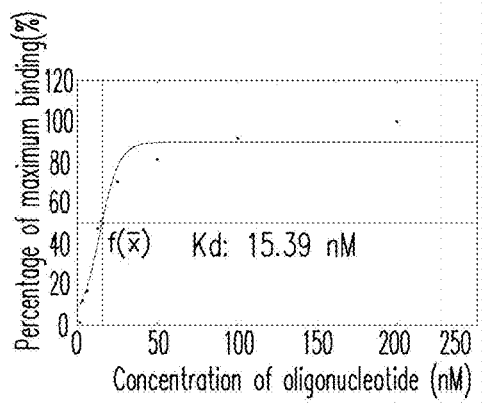
Figure 13F:
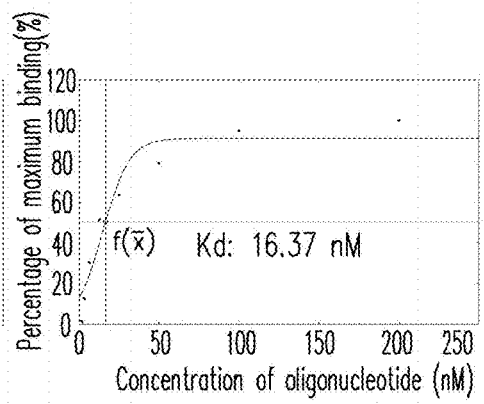

FIG. 12 shows the results of cross-reactions between the K1-1 for CRP, K2-4 for HBs Ag, and K3-1 for HCV NS3, which have the lowest cross-reaction. In FIG. 12, the hollow columns give the relative expression levels from q-PCR of the input controls and the solid columns give the relative expression levels of the aptamers remained in the sample after removal of hybridized aptamers. The level of cross-reaction was calculated by substracting the expression level of the reaction from that of the input control, dividing the result by that of the input control and multiplying by 100%. The cross-reactions were 5.66%, 11.89%, and 15.18% for K3-1 vs. K1-1, K3-1 vs. K2-4, and K2-4 vs. K1-1, respectively. After the completion of the reverse validation and cross-reaction experiment, the plasmids of selected aptamers, K1-1 for CRP, K2-4 for HBs Ag, and K3-1 for HCV NS3, picked form the cloning process, were sequenced and the sequences of the 20N region of the aptamers screened by window-MARAS are listed in Table 2. For further experiments, the aptamers, K1-1, K2-4, and K3-1, were chemical synthesized and purchased from MDBio. The cross reaction will reduce the assaying efficacy of the aptamers forming the reagent in multiplex immunoassay and the higher the cross-reaction does the smaller the dynamic range is for the aptamer-based reagent in assaying multiple target analytes. It is worthy to mention that the cross-reaction showed above is expected to be much lower during detection since it was obtained based on oliganucletide hybirdization without any target analytes presented. In detection, the competition from the target analytes will reduce the opportunity of aptamer hybridizing with another aptamer. Furthermore, the quantity of aptamers in reagents can be increased to account the loss of aptamer ligands due to the cross-reaction in order to maintain the desired dynamic range of detection.

| The sequences of 20N region of the MP-aptamers screened by window-MARAS | |
|---|---|
| Aptamer clone name | Target sequence |
| K1-1 (SEQ ID NO: 11) | CCTAACGATGCGACATGGGG |
| K2-4 (SEQ ID NO: 12) | CCAACCGGAATCTGCACCTC |
| K3-1 (SEQ ID NO: 13) | CCCATGTCCACCTTTCTGTG |

Determination of Equilibrium Dissociation Constants by q-PCR

The affinities of the K1-1, K2-4, and K3-1 aptamers toward the CRP, HBs Ag, and HCV NS3 target analytes, respectively, were described by the equilibrium dissociation constants (Kd), which were measured by q-PCR. For K1-1 aptamer vs. CRP target analyte, a series of progressively diluted K1-1 aptamers (200 nM to 1.5625 nM) in 20 μl of BD buffer were heated to 95° C. for 5 minutes and cooled at 4° C. for the formation of secondary structures. Partial diluted aptamers were retained as an input control (input). CRP-MNPs (P1), obtained from 5 μl of CRP-MNP reagent by magnetic separation, were added into each micro-tube containing diluted K1-1 aptamers and incubated for 30 minutes at room temperature. A magnetic separation was performed to collect the bound mixture. The bound mixtures were washed twice with 100 μl of BD buffer. The bound aptamers were eluted from the CRP-MNPs by heating at 94° C. for 10 minutes in 20 μl of ddH$_2$O. The CRP-MNPs in the solution were removed with a magnetic stand, and the supernatants were collected. Both the input control and eluted aptamers were precipitated with 1 ml of 100% ice-cold alcohol. The input control and eluted aptamers were individually dissolved into test tubes filled with 100 μl of ddH$_2$O. The quantities of the aptamers in each test tube, including input control tube and eluted aptamer tubes, were calculated by q-PCR as described before. The q-PCR analysis was performed with MicroAmp optical 96-well reaction plates, and the threshold cycle (ct) value was calculated automatically using the maximum correlation coefficient approach with StepOnePlus Real-Time PCR Systems software, version 2.0 (Applied Biosystems). The concentrations of the K1-1 aptamers in the input control and the eluted aptamers were calculated, using a 200 nM concentration of aptamers as indicative of maximum binding. The Kd value of the K1-1 aptamer toward CRP was then determined by fitting a saturation binding curve based on the experimental data via a curve fitting program, CurveExpert1.3 (curveexpert.webhop.net). The Kd value of the K1-1 aptamer toward CRP was performed in duplicate for each q-PCR run and was expressed as the mean±standard deviation from three separate experiments performed. The same procedure was repeated for the determination of the Kd values of K2-4, and K3-1 aptamers using HBs Ag, and HCV NS3 target analytes, respectively.

The representative fitting curves and the detail results of dissociation constants of K1-1, K2-4, and K3-1 aptamers are shown in FIG. 13A-13F. FIG. 13A-13F show the equilibrium dissociation constants equivalent dissociation constants of Aptamer K1-1, K2-4, and K3-1 toward different target analytes; and the aptamers vs. target analytes are as follows, FIG. 13A-13B: K1-1 vs. CRP, FIG. 13C-13D: K2-4 vs. HBs Ag, and FIG. 13E-13F: K3-1 vs. HCV NS3 protein. The results show that the value of Kd of K1-1 aptamer for CRP is 38.47±0.30 nM, K2-4 aptamer for HBs Ag is 31.41±0.62 nM, and K3-1 for HCV NS3 is 15.88±0.69 nM. The results indicate that the selected K1-1, K2-4, and K3-1 aptamers were capable of binding with corresponding target analytes and can be used for multiplex immunoassays. The values of the dissociation constant of K1-1 vs. CRP, K2-4 vs. HBs Ag, and K3-1 vs. HCV NS3 decreased sequentially. The sequential decrease of the dissociation constant of K1-1, K2-4, and K3-1 aptamers toward their corresponding target analytes were attributed to the enhancement of competitive mechanism induced by the increase of magnetic field frequency for these three aptamers during screening process.

Establishment of Standard Calibration Curve by q-PCR

Figure 14A:
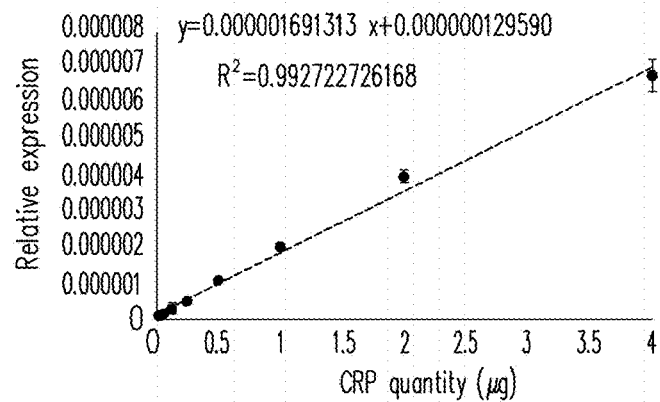
FIG. 14A-14C show the standard calibration curve for target analytes using K1-1, K2-4, and K3-1 aptamers as capture ligands by q-PCR analysis, the relative expression level of K1-1 vs. CRP, K2-4 vs. HBs Ag, and K3-1 vs. HCV NS3 quantities in BD buffer, respectively.
Figure 14B:
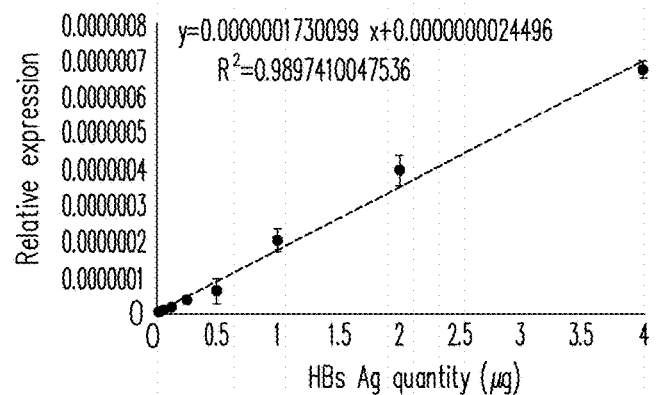
Figure 14C:
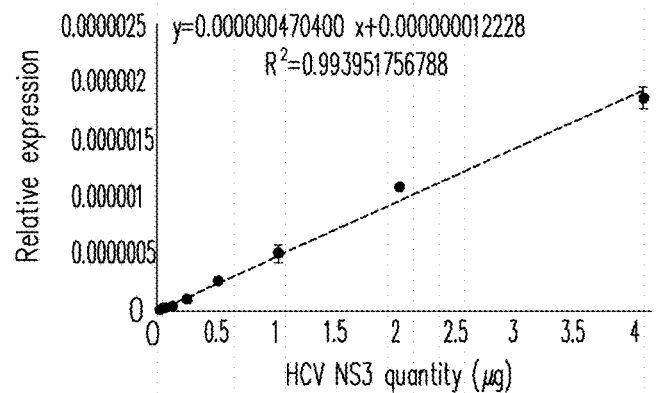
Figure 15A:
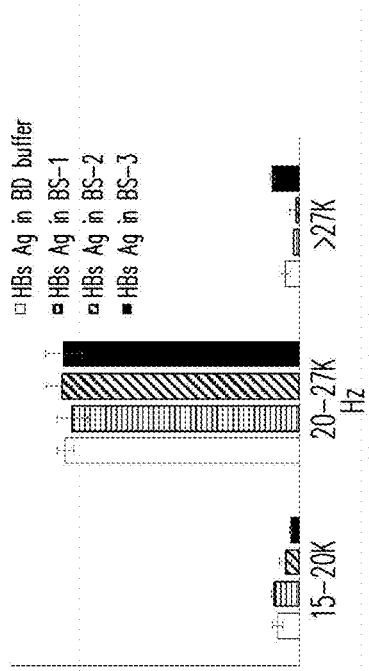
FIG. 15A-15D show the recovered quantities of target analytes in samples using the reagent containing K1-1, K2-4, and K3-1 aptamers as capture ligands according to some embodiments of the present invention.
Figure 15B:
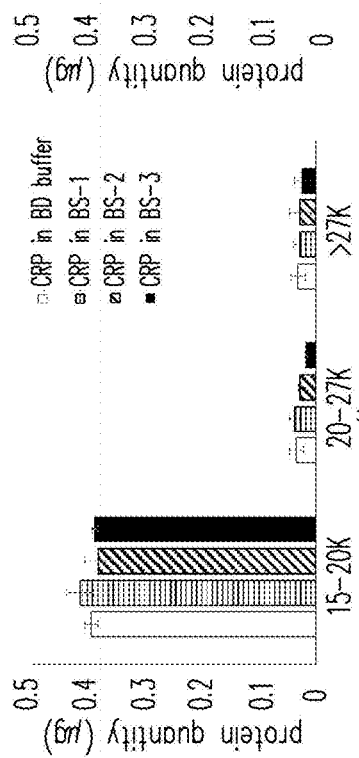
Figure 15C:
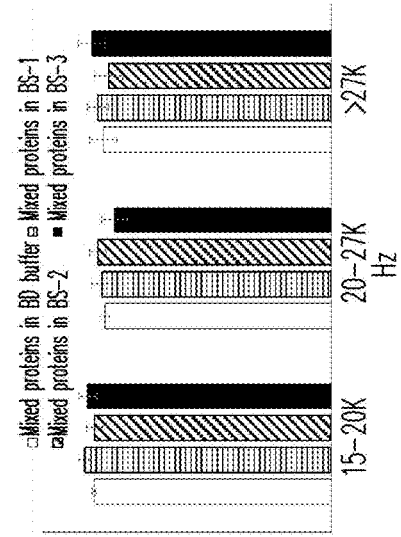
Figure 15D:
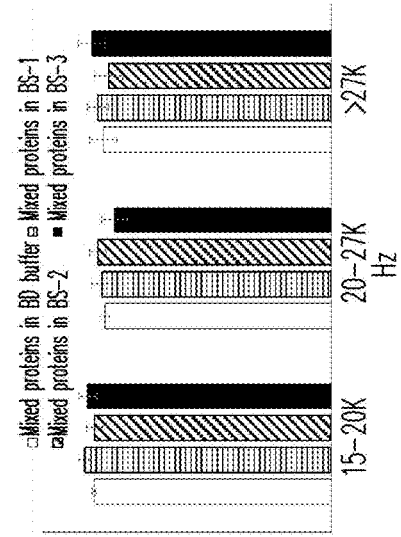

Standard calibration curves were individually determined by using a serial dilution of CRP-MNPs, HBs Ag-MNPs, and HCV NS3-MNPs, obtained from 1 µl of CRP-MNP (P1), HBs Ag-MNP (P2), and HCV NS3-MNP (P3) reagents by magnetic separation, respectively, in micro-tubes containing 10 µl BD buffer. Similar process steps as described above are omitted herein. Standard calibration curves for target analytes using K1-1, K2-4, and K3-1 aptamers as capture ligands by q-PCR are obtained and linear relationships of the relative expression level versus the quantities of CRP, HBs Ag, and HCV NS3, respectively, in samples are obtained. The result of the standard calibration curves for the q-PCR expression levels of K1-1, K2-4, and K3-1 aptamers as functions of quantities of CRP, HBs Ag, and HCV NS3 target analytes in the samples is shown in FIG. 14A-14C, respectively.

Determination of Recovery Rate Using Reagent Containing K1-1, K2-4, and K3-1 Aptamers as Capture Ligands in Assaying Target-Spiked Human Serums Three volunteer's blind serums were used as blind samples for the determination of recovery rate of MP-aptamers as capture ligands, of which CRP, HBs Ag, and HCV NS3 concentrations were undetectable, named as: blind serum-1 (BS-1), -2 (BS-2), and -3 (BS-3). The preparation of blind serum MNPs is as described in material section. A mixed protein MNPs was prepared by mixing equal amount (1.6 µg protein each) of CRP, HBs Ag, and HCV NS3 MNPs, obtained from 0.4 µl of corresponding MNP reagent by magnetic separation, and was then spiked into 40 µl BD buffer to form mixed protein MNP solution. One quarter of the mixed protein MNP solution, including CRP, HBs Ag, and HCV NS3, was named as "Mixed proteins in BD buffer". The remaining portion was equally divided into three parts, of which each part was individually spiked with blind serum MNPs (BS-1, BS-2, and BS-3) obtained from 0.1 µl of corresponding blind serum MNP reagents through magnetic separation, respectively, and named as "Mixed proteins in BS-1", "Mixed proteins in BS-2", and "Mixed proteins in BS-3". A 5000 nM of K1-1, K2-4, and K3-1 aptamers was heated to 95° C. for five minutes and cooled at 4° C. for the formation of secondary structures, individually, and then mixed to form "Mixed aptamer reagent" in the BD buffer. A 20 µl of "Mixed aptamer reagent" was incubated with protein MNPs, obtained from the "Mixed proteins in BD buffer" solution by magnetic separation, for 30 minutes at room temperature. The supernatant was removed by magnetic stand and the bound mixture was collected and dispersed in 100 µl BD buffer. The bound mixture solution in a micro-tube was placed inside RO-MARAS platform and subjected to an initial window-MARAS condition with field frequency of 15 KHz for 10 minutes at room temperature. A magnetic separation was performed to remove the supernatant and 100 µl BD buffer was added to disperse the retained bound mixture. The bound mixture solution was then subjected to a second window-MARAS condition with field frequency of 20 KHz for 10 minutes at room temperature. A magnetic separation was performed to collect the supernatant and named as "15-20 KHz". A 100 µl BD buffer was added to disperse the retained bound mixture. The bound mixture solution was finally subjected to the third window-MARAS condition with frequency of 27 KHz for 10 minutes at room temperature. A magnetic separation was performed to collect the supernatant and named as "20-27 KHz". A 100 µl BD buffer was added to disperse the retained bound mixture. The bound mixture solution was heated at 94° C. for 10 minutes to elute aptamers from the MNPs. A magnetic separation was performed to collect the supernatant and named as ">27 KHz". All the collected supernatants, "15-20 KHz", "20-27 KHz", and ">27 KHz", were precipitated with 1 ml of 100% ice-cold alcohol and individually dissolved in test tubes filled with 100 µl of ddH$_2$O. The amount of oligonucleotides in each test tube was analyzed by q-PCR in duplicate as described before and calculated via the corresponding linear equation of the standard calibration curves to determine the CRP, HBs Ag, and HCV NS3 quantities in "Mixed proteins in BD buffer". The same procedure was repeated for "Mixed proteins in BS-1", "Mixed proteins in BS-2", and "Mixed proteins in BS-3". Furthermore, the same procedure was also applied to single target analyte by using CRP-MNPs, HBs Ag-MNPs, or HCV NS3-MNPs, to replace the mixed protein MNPs. By using CRP as an example, CRP-MNPs (1.6 µg CRP), obtained from 0.4 µl of CRP-MNP reagent by magnetic separation, was spiked into 40 µl BD buffer. One quarter (10 µl) of the CRP-MNP solution was named as "CRP in BD buffer". The remaining portion was equally divided into three parts, of which each part was individually spiked with blind serum MNPs, obtained from blind serum-1 (BS-1), -2 (BS-2), and -3 (BS-3) by magnetic separation, respectively, and named as "CRP in BS-1", "CRP in BS-2", and "CRP in BS-3". Following the same procedure described above, the quantity of spiked CRP in "CRP in BD buffer", "CRP in BS-1", "CRP in BS-2", and "CRP in BS-3" can be determined using the "Mixed aptamer reagent" via the CRP standard calibration curve.

The result of recovered quantities of target analytes in various samples using the "Mixed aptamer reagent" made of K1-1, K2-4, and K3-1 aptamers as capture ligands was shown in FIGS. 15A-15D and the corresponding recovery rates were listed in Table 3. FIGS. 15A-15D show the recovered quantities of target analytes in samples using K1-1, K2-4, and K3-1 aptamers as capture ligands, whereas the target analytes are CRP in FIG. 15A, HBs Ag in FIG. 15B, HCV NS3 protein in FIG. 15C, and mixed proteins in FIG. 15D. In Table 3, the recovery rate was calculated based on the quantity of spiked target analytes, which was 0.4 µg each ideally, and was between 94.19% and 107.17%. The K1-1, K2-4 and K3-1 aptamers could bind to corresponding target analytes under the upper-bound frequency of window-MARAS. For example, K1-1 aptamer binds to CRP-MNPs in "CRP in BD buffer" sample under the frequency of 20 KHz. When the rotating magnetic field frequency was higher than upper-bound (>20K Hz), K1-1 aptamer was detached from the CRP-MNPs. The same result was obtained for the rotating magnetic field frequency of 27 KHz. The amount of K1-1 aptamers bound to CRP-MNPs was measured by q-PCR and the quantity of CRP was calculated via the standard calibration curve of CRP. It is noted that the frequency range of the applied rotating magnetic field during detection stage is the same as that used in the aptamer-generating stage. The results of K2-4 and K3-1 aptamers were similar to that of K1-1, except the frequency range of the applied rotating magnetic field. Furthermore, there is no significant difference between the recovered protein quantities by using mixed protein MNPs instead of pure protein MNPs in the samples. For using mixed protein MNPs, the protein recovery rate was similar under different magnetic frequency ranges as comparing to that of using single protein MNPs. The result reveals that during the detection stage, the interference from multiple target analytes in the sample has a minimal effect. It is noted that theoretically the levels of recovered target proteins in serums should be equal or higher than that in BD buffer due to nonspecific binding as proteins presented in serums other than target analytes and the deviation can be attributed to the experimental error magnified by q-PCR. However, by comparing the results with or without the blind human serums, it reveals that there is a limited interference from proteins in the blind serums other than target proteins. This result clearly illustrates that the K1-1, K2-4, and K3-1 aptamers could specific bind to CRP, HBs Ag, and HCV NS3, respectively in BD buffer and human serums and the reagent made of these three aptamers can be used for multiplex immunoassay to detect the concentration of CRP, HBs Ag, and HCV NS3 proteins in a single assay.

TABLE 3

| (%) | Target in BD buffer | Target in BS-1 | Target in BS-2 | Target in BS-3 |
|---|---|---|---|---|
| CRP (15-20 KHz) | 99.31 | 104.12 | 96.24 | 97.60 |
| HBs Ag (20-27 KHz) | 101.38 | 98.29 | 102.66 | 102.18 |
| HCV NS3 (>27 KHz) | 103.62 | 100.40 | 97.69 | 98.19 |
| Mixed proteins (15-20 KHz) | 102.88 | 107.17 | 102.88 | 105.74 |
| Mixed proteins (20-27 KHz) | 98.23 | 99.58 | 101.29 | 94.19 |
| Mixed proteins (>27 KHz) | 98.87 | 101.17 | 96.61 | 103.97 |

The above results verify that aptamers capable of binding to a specific target analyte with desired affinity are screened from a random oligonucleotide library using window-MARAS procedure with a designated field frequency range of the applied rotating magnetic field. By altering the frequency range, aptamers capable of binding to the specific analytes with differential affinities are obtained. The obtained aptamers can be used as the capture ligands in reagents capable of binding to multiple target analytes in multiplex immunoassays. By applying the same magnetic field condition during detection stage, the quantities of different analytes in the sample can be identified by q-PCR. The interference from other molecules in the samples other than the target analytes is minimized by performing the negative selection, such as multiple negative selection cycles and extra negative selections. From these results, it is suggested that if the aptamers having the desirable Kd toward analytes are obtained (i.e. affinities between capture ligands and analytes being controlled within desired ranges), multiplex immunoassays using such aptamers as capture ligands in reagents are able to detect analytes through the differential affinity. These assays are particularly useful for the disease diagnosis in clinical applications which only the concentrations of few biomarkers in patient's serum are needed to be identified.

In summary, a multiplex immunoassay technology is presented and demonstrated by utilizing differential affinity among capture ligand(s) (selected aptamers) and its (their) corresponding target analytes. The obtained aptamer(s) selected by using the window-MARAS method is capable of binding to multiple analytes with differential affinities by altering the magnetic field condition during aptamer selection process. Moreover, one or more aptamers specific to and having a pre-estimated binding affinity to a target analyte (i.e. having the dissociation constant within a desirable range) can be selected by properly choosing a lower-bound and an upper-bound field frequencies and/or field strengths of the applied oscillating magnetic field of the window-MARAS methods. Furthermore, the reagents comprised of the obtained aptamers can be used for multiplex immunoassays. By applying the same field condition during detection stage using the aptamer-based reagents, the quantities of different target analytes in the sample can be identified via q-PCR or ELISA. It is worthy to mention that all parameters affecting the competitive mechanism and affinity differentiating mechanism, such as the frequency and/or strength of the applied oscillating magnetic field as well as the size of magnetic particles, should be remained the same during the aptamer generating stage and the detection stage of multiplex immunoassay in order to have the same stretch forces against the bonds between the aptamers and target analytes, which are generated by the rotational or oscillating motion of magnetic particles in an aqueous solution, induced by the magnetic driving force and the dissipative force as the magnetic field acting on the dipole moment of magnetic particles. Furthermore, the architect of magnetic particle bound complexes used in this invention, including in the aptamer generating stage and detection stage, is aptamer-analyte-magnetic particle, if the architect is altered during the detection stage, such as analyte-aptamer-magnetic particle, the stretch force will change due to the size of the outmost component in the architect (the size of aptamer is much less than that of analyte) resulted from the higher dissipative force generated by the outmost component with a larger size. Therefore, if the size of the magnetic particles and the architect of magnetic particle bound complexes used in detection stage differ from those used in aptamer generation stage, then the magnetic field condition for the affinity differentiating mechanism must be determined experimentally prior to the multiplex immunoassays. The interference from the molecules in the samples other than the target analytes can be minimized by carefully designing the negative selection, such as multiple negative selection cycles. The results infers that if the affinity between capture ligands and analytes can be controlled at desired range, then it is possible to synthesize reagent capable of performing multiplex immunoassay utilizing the differential affinity, particularly for the disease diagnosis in clinical applications which only the concentrations of few biomarkers in patient's serum are needed to be identified.

What is claimed is:

1. A method of selecting aptamers, wherein each selected aptamer can bind to a plurality of different target analytes (i), comprising:
   a) providing a library of oligonucleotides with random nucleotide sequences denoted a random sequence library and heating and quenching the random sequence library to incude the formation of the secondary structure;
   b) preparing a plurality of magnetic particles conjugated with negative samples (j) (NS-MPs$_{(j)}$), wherein the magnetic particles (MPs) are nanoparticles (MNPs) or microparticles (MMPs), and wherein j is a variable integer with a value from 1 to J and each type of J types of negative samples (j) is a different type of negative sample from the others;
   c) incubating the random sequence library, from step a) if j equals one or from step d) of the preceding round if j is greater than one, with the NS-MPs$_{(j)}$ in a first binding buffer, wherein the random sequence library is incubated with each different NS-MPs$_{(j)}$ one by one, or the random sequence library is incubated with all of the different NS-MPs$_{(j)}$ in one batch, to allow oligonucleotides to bind to the NS-MPs$_{(j)}$;
   d) removing oligonucleotides bound to the NS-MPs$_{(j)}$ by performing a first magnetic separation using a magnetic stand and collecting a supernatant containing oligonucleotides not bound to the NS-MPs$_{(j)}$ for step e) if j equals J or as a random sequence library for step c) of a following round if j is less than J, wherein the process steps c) and d) are performed J times if in step c) the random sequence library is incubated with the different NS-MPs$_{(j)}$ one by one and j increases with an increment of one for a following round during repetition or if in step c) the random sequence library is incubated with all of the different NS-MPs$_{(j)}$ in one batch, the process steps c) and d) are performed once;
   e) preparing a plurality of magnetic particles conjugated with target analytes (i) (PS-MPs$_{(i)}$ and incubating the supernatant containing oligonucleotides, from step d) if i equals one or from step i) of the preceding round if i is greater than one, with the PS-MPs$_{(i)}$ to form a bound mixture containing oligonucleotides bound to PS-MPs (i), wherein the magnetic particles (MPs) are MNPs or MMPs and i is a variable integer with a value from 1 to I;
   f) collecting the bound mixture containing oligonucleotides bound to the PS-MPs$_{(i)}$ by performing a second magnetic separation using the magnetic stand, removing a supernatant containing oligonucleotides not bound to the PS-MPs(i), and redispersing the collected bound mixture containing oligonucleotides bound to the PS-MPs$_{(i)}$ in a second binding buffer;
   g) subjecting the redispersed bound mixture obtained in step f) to a window-MARAS in a first oscillating magnetic field with a lower-bound frequency f$_{iL}$ and/or a lower-bound strength H$_{iL}$ to detach oligonucleotides with a first binding affinity toward the PS-MPs$_{(i)}$ from the PS-MPs$_{(i)}$, and then removing a supernatant containing the oligonucleotides detached from the PS-MPs$_{(i)}$ and collecting the remaining bound mixture containing oligonucleotides bound to the PS-MPs$_{(i)}$ by performing a third magnetic separation using the magnetic stand;
   h) redispersing the collected bound mixture obtained in step g) in a third binding buffer;
   i) subjecting the redispersed bound mixture obtained in step h) to a window-MARAS at a second oscillating magnetic field with an upper-bound frequency f$_{iU}$ and/or an upper bound strength H$_{iU}$ to detach oligonucleotides with a second binding affinity toward the PS-MPs$_{(i)}$ from the PS-MPs$_{(i)}$, and then collecting a supernatant containing the oligonucleotides with the second binding affinity toward the PS-MPs$_{(i)}$ for step j) if i equals I or for step e) of a following round if i is less than I and removing oligonucleotides bound to the PS-MPs$_{(i)}$ with a third binding affinity toward the PS-MPs$_{(i)}$ by performing a fourth magnetic separation using the magnetic stand,
   wherein the process steps e)-i) are repeated as one round for I times or the process steps e)-i) are repeated as one round for (I-1) times and followed by performing the process steps e)-h) once, eluting the oligonucleotides having a binding affinity toward the PS-MPs$_{(i)}$ stronger than the first binding affinity toward the PS-MPs$_{(i)}$ out of the PS-MPs$_{(i)}$, collecting a supernatant containing the oligonucleotides having a binding affinity toward the PS-MPs$_{(i)}$ stronger than the first binding affinity toward the PS-MPs$_{(i)}$ for step j) by performing a fifth magnetic separation using the magnetic stand, wherein the second binding affinity is stronger than the first binding affinity and the third binding affinity is stronger than the second binding affinity, and wherein f$_{iL}$<f$_{iU}$≤f$_{(i+1)L}$ and/or H$_{iL}$<H$_{iU}$≤H$_{(i+1)L}$, i increases with an increment of one for a following round during repetition, and each type of I types of target analytes (i) is a different type of target analyte from the others; and
   j) obtaining oligonucleotides capable of conjugating with PS-MPs(i) that are aptamers that can bind to I types of different target analytes (i).

2. The method of claim 1, wherein step b) comprises:
   pre-treating a plurality of biological samples to remove interference target analytes (i) from the samples to make negative samples (j), or directly using a plurality of biological samples with a low concentration of interference target analytes (i) as negative samples (j) and conjugating the negative samples (j) with the magnetic particles to form the NS-MPs$_{(j)}$; and
   step e) comprises:
   providing the target analytes (i) and conjugating the target analytes (i) with the magnetic particles to form the PS-MPs$_{(i)}$.

3. The method of claim 2, wherein conjugating the negative samples (j) or the target analytes (i) with the magnetic particles comprises joining the negative samples (j) or the target analytes (i) to the magnetic particles through joining pairs respectively attached to the magnetic particles and negative samples (j) or the target analytes (i).

4. The method of claim 3, wherein the joining pairs are constituted by streptavidin and biotin, and wherein the streptavidin binds with the magnetic particles and the biotin binds with the negative samples (j) or the target analytes (i).

5. The method of claim 1, wherein step g) subjecting the redispersed bound mixture to a window-MARAS at a first oscillating magnetic field with a lower-bound frequency f$_{iL}$ and/or a lower-bound strength H$_{iL}$ comprises performing a magnetic-assisted screening by applying a first rotating magnetic field or a first alternating magnetic field with the lower-bound frequency f$_{iL}$ and/or the lower-bound strength H$_{iL}$.

6. The method of claim 1, wherein step i) subjecting the redispersed bound mixture to a window-MARAS at a second oscillating magnetic field with an upper-bound frequency $f_{iU}$ and/or an upper-bound strength $H_{iU}$ comprises performing a magnetic-assisted screening by applying a second rotating magnetic field or a second alternating magnetic field with the upper-bound frequency $f_{iU}$ and/or the upper-bound strength $H_{iU}$.

7. A method of selecting aptamers comprising:
 a) providing a library of oligonucleotides with random nucleotide sequences denoted a random sequence library and heating and quenching the random sequence library to induce the formation of secondary structure;
 b) preparing a plurality of magnetic particles conjugated with negative samples (j) (NS-MPs$_{(j)}$), wherein the magnetic particles (MPs) are nanoparticles (MNPs) or microparticles (MMPs), j is a variable integer with a value from 1 to J and each type of J types of negative samples (j) is a different type of negative sample from the others;
 c) incubating the random sequence library, from step a) if j equals one or from step d) of the preceding round if j is greater than one, with the NS-MPs$_{(j)}$ in a first binding buffer, wherein the random sequence library is incubated with each different NS-MPs$_{(j)}$ one by one, or the random sequence library is incubated with all of the different NS-MPs$_{(j)}$ in one batch, to allow oligonucleotides to bind to the NS-MPs$_{(j)}$;
 d) removing a bound mixture containing oligonucleotides bound to the NS-MPs$_{(j)}$ by performing a first magnetic separation using a magnetic stand and collecting a supernatant containing oligonucleotides not bound to the NS-MPs$_{(j)}$ for step e) if j equals J or as a random sequence library for step c) of a following round if j is less than J, wherein the process steps c) and d) are performed J times if in step c) the random sequence library is incubated with the different NS-MPs$_{(j)}$ one by one and j increases with an increment of one for a following round during repetition, or if in step c) the random sequence library is incubated with all of the different NS-MPs$_{(j)}$ in one batch, the process steps c) and d) are performed once;
 e) preparing a plurality of magnetic particles conjugated with auxiliary target analytes (k) (PS-MPs$_{(k)}$), and incubating the supernatant containing oligonucleotides, from step d) if k equals one or from step f) of the preceding round if k is grater than one, with the PS-MPs(k), wherein the magnetic particles (MPs) and MNPs or MMPs, and wherein k is a variable integer with a value from 1 to K, each type of K types of auxiliary target analytes (k) is a different type of auxiliary target analyte from the others, and the collected supernatant is incubated with each different PS-MPs$_{(k)}$ one by one, or the collected supernatant is incubated with all of the different PS-MPs$_{(k)}$ in one batch, to allow oligonucleotides to bind to the PS-MPs$_{(k)}$;
 f) removing the bound mixture containing oligonucleotides bound to the PS-MPs$_{(k)}$ by performing a second magnetic separation using the magnetic stand and collecting a supernatant containing oligonucleotides not bound to the PS-MPs(k) for step g) if k equals K or for step e) of a following round if k is less than K, wherein the process steps e) and f) are repeated K times if in step e) the collected supernatant is incubated with each different PS-MPs$_{(k)}$ one by one nd k increases with an increment of one for a following round during repetition, or if in step e) the collected supernatant is incubated with all of the different PS-MPs$_{(k)}$ in one batch, the process steps e) and f) are performed once;
 g) preparing a plurality of magnetic particles conjugated with a single type of main target analytes (i) (PS-MPs$_{(i)}$), and incubating the supernatant collected in step f) with the PS-MPs(i) to form a bound mixture, wherein the magnetic particles are MNPs or MMPs, and wherein i is a variable integer with a value from 1 to I, and the single type of main target analytes (i) is different from each type of the auxiliary target analytes;
 h) collecting the bound mixture containing oligonucleotides bound to the PS-MPs$_{(i)}$ by performing a third magnetic separation using the magnetic stand and removing a supernatant containing oligonucleotides unbound with the PS-MPs$_{(i)}$;
 i) redispersing the collected bound mixture obtained in step h) in a second binding buffer;
 j) subjecting the redispersed bound mixture from step i) to a window-MARAS at a first oscillating magnetic field with a lower-bound frequency $f_{iL}$ and/or a lower-bound strength $H_{iL}$ to detach oligonucleotides with a first binding affinity toward the PS-MPs$_{(i)}$ from the PS-MPs (i), and then removing a supernatant containing the oligonucleotides detached from the PS-MPs$_{(i)}$ and collecting the bound mixture containing oligonucleotides bound to the PS-MPs$_{(i)}$ by performing a fourth magnetic separation using the magnetic stand;
 k) redispersing the bound mixture obtained in step j) in a third binding buffer;
 l) subjecting the redispersed bound mixture obtained in step k) to a window-MARAS at a second oscillating magnetic field with an upper-bound frequency $f_{iU}$ and/or an upper-bound strength $H_{iU}$ to detach oligonucleotides with a second binding affinity toward the PS-MPs$_{(i)}$ from the PS-MPs$_{(i)}$, and then collecting a supernatant containing oligonucleotides with the second binding affinity toward the PS-MPs$_{(i)}$ for step m) and removing the oligonucleotides bound to the PS-MPs$_{(i)}$ with a third binding affinity toward the PS-MPs$_{(i)}$ by performing a fifth magnetic separation using the magnetic stand,
 wherein the process steps a) to l) are repeated as one round for I times, or the process steps a) to l) are repeated as one round for (I-1) times and followed by performing the process steps a) to k) once, eluting the oligonucleotides having a binding affinity toward the PS-MPs$_{(i)}$ stronger than the first binding affinity toward the PS-MPs$_{(i)}$ out of the PS-MPs$_{(i)}$, and collecting a supernatant containing the oligonucleotides having a binding affinity toward the PS-MPs$_{(i)}$ stronger than the first binding affinity toward the PS-MPs$_{(i)}$ for step m) by performing a sixth magnetic separation using the magnetic stand, i increases with an increment of one for a following round during repetition, and each type of I types of main target analytes (i) is a different type of main target analyte from the others, wherein the second binding affinity is stronger than the first binding affinity and the third binding affinity is stronger than the second binding affinity, and wherein $f_{iL} < f_{iU} \leq f_{(i+1)L}$ and/or $H_{iL} < H_{iU} \leq H_{(i+1)L}$; and
 m) obtaining oligonucleotides capable of conjugating with PS-MPs$_{(i)}$ as aptamers binding to target analytes, wherein a single type of aptamers only binds to a single type of target analytes (i) and the binding affinity between each type of aptamer and its corresponding type of target analyte (i) is different from the others.

8. The method of claim 7, wherein step b) comprises pre-treating a plurality of biological samples to remove interference target analytes (i) from samples as negative samples (j) or directly using a plurality of biological samples with a low concentration of interference target analytes (i) as negative samples (j) and conjugating the negative samples (j) with the magnetic particles to form the NS-MPs$_{(j)}$;

step e) comprises providing the auxiliary target analytes (k) and conjugating the auxiliary target analytes (k) with the magnetic particles to form the PS-MPs$_{(k)}$; and step g) comprises providing the main target analytes (i) and conjugating the main target analytes (i) with the magnetic particles to form the PS-MPs$_{(i)}$.

9. The method of claim 8, wherein conjugating the negative samples (j), the auxiliary target analytes (k) or the main target analytes (i) with the magnetic particles comprises joining the negative samples (j), the auxiliary target analytes (k) or the main target analytes (i) to the magnetic particles through joining pairs respectively attached to the magnetic particles and the negative samples (j), the auxiliary target analytes (k) or the main target analytes (i).

10. The method of claim 9, wherein the joining pairs are constituted by streptavidin and biotin, and wherein the streptavidin binds with the magnetic particles and the biotin binds with the negative samples (j), the auxiliary target analytes (k) or the main target analytes (i).

11. The method of claim 7, wherein step j) subjecting the redispersed bound mixture to a window-MARAS at a first oscillating magnetic field with a lower-bound frequency $f_{iL}$ and/or a lower-bound strength $H_{iL}$ comprises performing a magnetic-assisted screening by applying a first rotating magnetic field or a first alternating magnetic field with the lower-bound frequency $f_{iL}$ and/or the lower-bound strength $H_{iL}$.

12. The method of claim 7, wherein step l) subjecting the redispersed bound mixture to a window-MARAS at a second oscillating magnetic field with an upper-bound frequency $f_{iU}$ and/or an upper-bound strength $H_{iU}$ comprises performing a magnetic-assisted screening by applying a second rotating magnetic field or a second alternating magnetic field with the upper-bound frequency $f_{iU}$ and/or the upper-bound strength $H_{iU}$.

* * * * *

SEQUENCE LISTING

```
<160> NUMBER OF SEQ ID NOS: 13

<210> SEQ ID NO 1
<211> LENGTH: 15
<212> TYPE: DNA
<213> ORGANISM: Artificial Sequence
<220> FEATURE:
<223> OTHER INFORMATION: Primer

<400> SEQUENCE: 1
agcagcacag aggtc                                                    15

<210> SEQ ID NO 2
<211> LENGTH: 15
<212> TYPE: DNA
<213> ORGANISM: Artificial Sequence
<220> FEATURE:
<223> OTHER INFORMATION: Primer

<400> SEQUENCE: 2
gcgtgctacc gtgaa                                                    15

<210> SEQ ID NO 3
<211> LENGTH: 15
<212> TYPE: DNA
<213> ORGANISM: Artificial Sequence
<220> FEATURE:
<223> OTHER INFORMATION: Primer

<400> SEQUENCE: 3
ttcacggtag cacgc                                                    15

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
taatacgact cactataggg                                               20

<210> SEQ ID NO 5
<211> LENGTH: 20
<212> TYPE: DNA
<213> ORGANISM: Artificial Sequence
<220> FEATURE:
<223> OTHER INFORMATION: Randomized synthesized DNA sequence

<400> SEQUENCE: 5
ctgcatcacg aagcctggca                                               20

<210> SEQ ID NO 6
<211> LENGTH: 20
<212> TYPE: DNA
<213> ORGANISM: Artificial Sequence
<220> FEATURE:
<223> OTHER INFORMATION: Randomized synthesized DNA sequence

<400> SEQUENCE: 6
aggtcctccg aatgggacta                                               20

<210> SEQ ID NO 7
<211> LENGTH: 20
<212> TYPE: DNA
<213> ORGANISM: Artificial Sequence
```

```
<220> FEATURE:
<223> OTHER INFORMATION: Randomized synthesized DNA sequence

<400> SEQUENCE: 7
ccggaacacc agaagcacgt                                                   20

<210> SEQ ID NO 8
<211> LENGTH: 20
<212> TYPE: DNA
<213> ORGANISM: Artificial Sequence
<220> FEATURE:
<223> OTHER INFORMATION: Randomized synthesized DNA sequence

<400> SEQUENCE: 8
cccgtcacct attttccgt                                                    20

<210> SEQ ID NO 9
<211> LENGTH: 20
<212> TYPE: DNA
<213> ORGANISM: Artificial Sequence
<220> FEATURE:
<223> OTHER INFORMATION: Randomized synthesized DNA sequence

<400> SEQUENCE: 9
acaggggaag aagcgtcacc                                                   20

<210> SEQ ID NO 10
<211> LENGTH: 20
<212> TYPE: DNA
<213> ORGANISM: Artificial Sequence
<220> FEATURE:
<223> OTHER INFORMATION: Randomized synthesized DNA sequence

<400> SEQUENCE: 10
ccttggcatg attgtctcct                                                   20

<210> SEQ ID NO 11
<211> LENGTH: 20
<212> TYPE: DNA
<213> ORGANISM: Artificial Sequence
<220> FEATURE:
<223> OTHER INFORMATION: Randomized synthesized DNA sequence

<400> SEQUENCE: 11
cctaacgatg cgacatgggg                                                   20

<210> SEQ ID NO 12
<211> LENGTH: 20
<212> TYPE: DNA
<213> ORGANISM: Artificial Sequence
<220> FEATURE:
<223> OTHER INFORMATION: Randomized synthesized DNA sequence

<400> SEQUENCE: 12
ccaaccggaa tctgcacctc                                                   20

<210> SEQ ID NO 13
<211> LENGTH: 20
<212> TYPE: DNA
<213> ORGANISM: Artificial Sequence
<220> FEATURE:
<223> OTHER INFORMATION: Randomized synthesized DNA sequence

<400> SEQUENCE: 13
cccatgtcca cctttctgtg                                                   20
```